(12) United States Patent
Cheronis

(10) Patent No.: US 6,777,403 B2
(45) Date of Patent: Aug. 17, 2004

(54) METHOD AND STRUCTURE FOR INHIBITING ACTIVITY OF SERINE ELASTASES

(75) Inventor: John C. Cheronis, Conifer, CO (US)

(73) Assignee: Cortech, Inc., Bedminster, NJ (US)

( * ) Notice: Subject to any disclaimer, the term of this patent is extended or adjusted under 35 U.S.C. 154(b) by 0 days.

(21) Appl. No.: 10/329,057

(22) Filed: Dec. 23, 2002

(65) Prior Publication Data

US 2003/0134856 A1 Jul. 17, 2003

Related U.S. Application Data

(62) Division of application No. 09/596,797, filed on Jun. 19, 2000, now Pat. No. 6,569,876.
(60) Provisional application No. 60/139,625, filed on Jun. 17, 1999.

(51) Int. Cl.$^7$ .................. A61K 31/33; A61K 31/505; A61K 38/00; C07D 239/02; C07D 265/28
(52) U.S. Cl. .................. 514/183; 514/19; 514/256; 514/269; 514/274; 514/398; 514/397; 544/98; 544/242; 544/309; 544/335; 544/336; 548/122
(58) Field of Search .................. 514/183, 19, 256, 514/269, 274, 398, 397, 364; 544/98, 242, 309, 335, 336; 548/122

(56) References Cited

U.S. PATENT DOCUMENTS

| | | | |
|---|---|---|---|
| 5,281,617 A | | 1/1994 | Kirschenheuter et al. |
| 5,424,293 A | | 6/1995 | Zoller et al. |
| 5,561,380 A | | 10/1996 | Sway-Tin et al. |
| 5,618,792 A | * | 4/1997 | Gyorkos et al. .............. 514/18 |
| 5,807,829 A | | 9/1998 | Gyorkos et al. |
| 5,861,380 A | | 1/1999 | Gyorkos et al. |
| 5,861,830 A | | 1/1999 | Cheng et al. |
| 5,869,455 A | | 2/1999 | Gyorkos et al. |
| 5,874,585 A | | 2/1999 | Gyorkos et al. |
| 5,891,852 A | * | 4/1999 | Gyorkos et al. .............. 518/18 |
| 5,998,379 A | | 12/1999 | Gyorkos et al. |
| 6,001,811 A | | 12/1999 | Gyorkos et al. |
| 6,001,813 A | | 12/1999 | Gyorkos et al. |
| 6,001,814 A | | 12/1999 | Gyorkos et al. |
| 6,015,791 A | | 1/2000 | Gyorkos et al. |
| 6,037,325 A | | 3/2000 | Gyorkos et al. |
| 6,100,238 A | | 8/2000 | Gyorkos et al. |
| 6,150,334 A | | 11/2000 | Gyorkos et al. |
| 6,159,938 A | | 12/2000 | Gyorkos et al. |

FOREIGN PATENT DOCUMENTS

| | | |
|---|---|---|
| EP | 0 528 633 A1 | 2/1993 |
| WO | WO 96/16080 | 5/1996 |
| WO | WO 98/24806 | 6/1998 |

OTHER PUBLICATIONS

Lorand, L. *Proteolytic Enzymes Part C*, Methods in Enzymology, vol. 80:535–561 (1981).
Brömme, et al. *The Specificity of Bovine Spleen Cathepsin S*, Biochem. J. 264:475–481 (1989).
Helm, et al. *Serine Elastases in Inflammatory and Vascular Diseases*, Protease as Targets for Therapy, Chapter 14, Handbook of Experimental Pharmacology, vol. 140:259–275.
International Search Report dated Oct. 13, 2000.
Wieczorek, et al. Biochemical Characterization of α–Ketooxadiazole Inhibitors of Elastases, *Archives of Biochemistry and Biophysics*, vol. 367, No. 2, Jul. 15, pp. 193–201, 1999.

* cited by examiner

Primary Examiner—Mukund J. Shah
Assistant Examiner—Sudhaker B. Patel
(74) Attorney, Agent, or Firm—Bromberg & Sunstein LLP

(57) ABSTRACT

Therefore, it is critical that the roles these enzymes play in biological processes outside of extracellular matrix degradation or remodeling be understood in order to assess their potential as targets for therapeutic intervention, and to design safe, conveniently produced, orally active inhibitors. Elastase inhibitors can differ with respect to their ability to inhibit different elastases. As a result, the spectrum of elastases inhibited by a specific drug candidate as well as the spectrum of activities these enzymes have with respect to proteins other than elastin are properties to consider in evaluating the drug candidates.

21 Claims, 34 Drawing Sheets

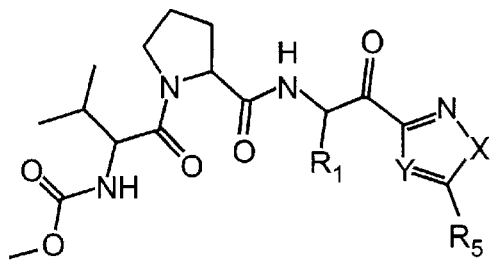
IF X=O, Y=N
IF X=N, Y=O
$R_1$=(-CH$_3$)
=(-CH$_2$CH$_3$)
=(-CH$_2$CH$_2$CH$_3$)
=(-CH$_2$CH$_2$CH$_2$CH$_3$)
=(-CH$_2$CH$_2$-S-CH$_3$)
=(-CH$_2$-S-CH$_3$)
=(-CH$_2$CH$_2$-O-CH$_3$)
=(-CH$_2$-O-CH$_3$) OR
=(-CH$_2$-O-CH$_2$CH$_3$)
$R_5$=(-CH$_3$)
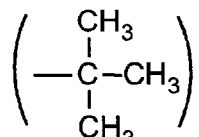
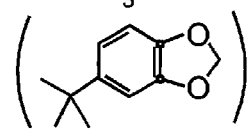
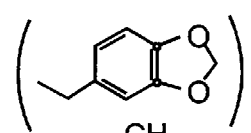
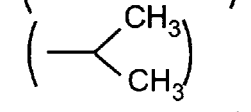
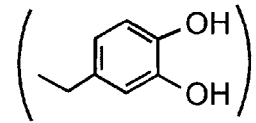
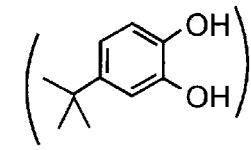
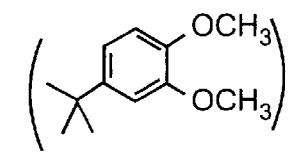
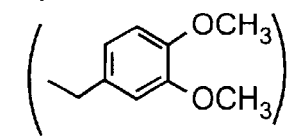
OR
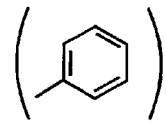
FIG. 3A-1

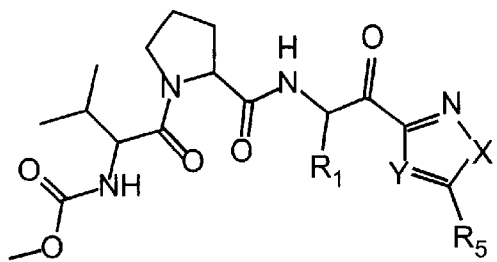
IF X=O, Y=N
IF X=N, Y=O
R_1=(-CH_3)
=(-CH_2CH_3)
=(-CH_2CH_2CH_3)
=(-CH_2CH_2CH_2CH_3)
=(-CH_2CH_2-S-CH_3)
=(-CH_2-S-CH_3)
=(-CH_2CH_2-O-CH_3)
=(-CH_2-O-CH_3) OR
=(-CH_2-O-CH_2CH_3)
R_5=(-CH_3)
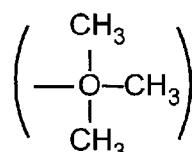
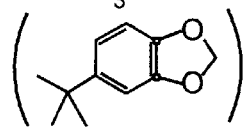
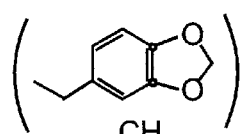
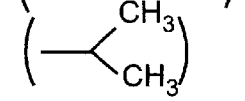
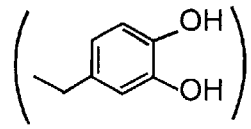
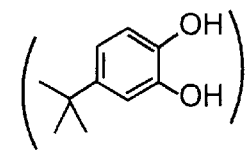
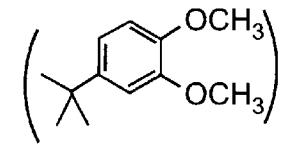
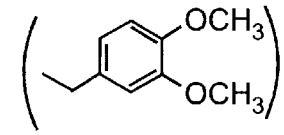
OR
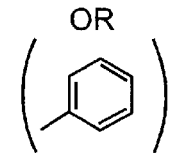
FIG. 3A-2

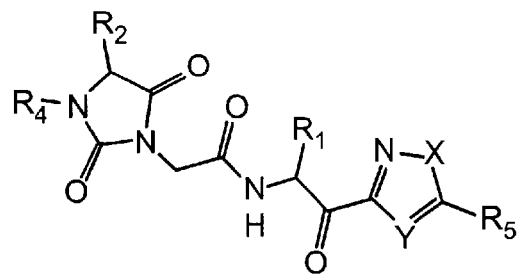
IF X=O, Y=N
IF X=N, Y=O
$R_5$=(-CH$_3$)
$R_1$=(-CH$_3$)
=(-CH$_2$CH$_3$)
=(-CH$_2$CH$_2$CH$_3$)
=(-CH$_2$CH$_2$CH$_2$CH$_3$)
=(-CH$_2$CH$_2$-S-CH$_3$)
=(-CH$_2$-S-CH$_3$)
=(-CH$_2$CH$_2$-O-CH$_3$)
=(-CH$_2$-O-CH$_3$) OR
=(-CH$_2$-O-CH$_2$CH$_3$)
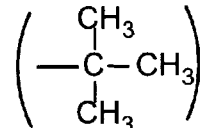
$R_2$=
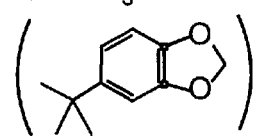
$R_4$=(H), OR
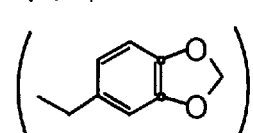
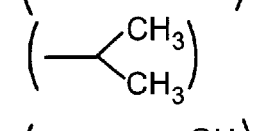
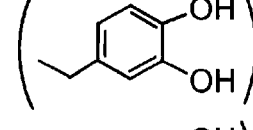
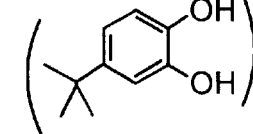
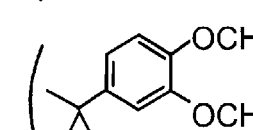
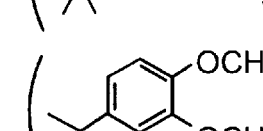
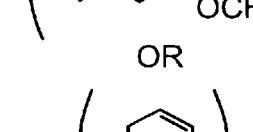
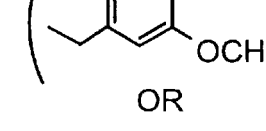
OR
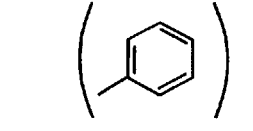
FIG. 3A-3

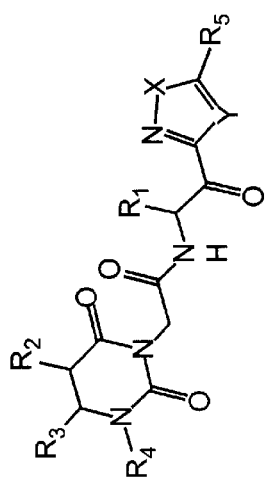
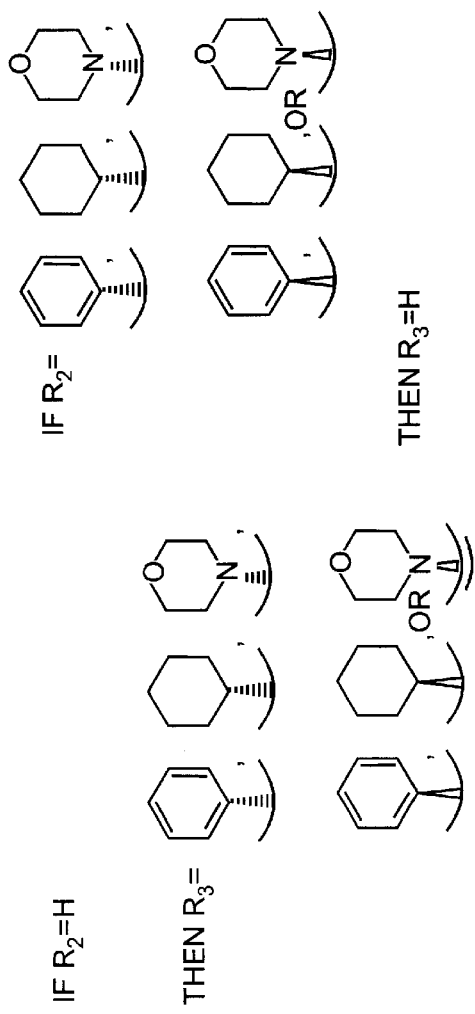
IF X=O, Y=N
IF X=N, Y=O
R₁=SAME AS FIG. 3A-3
R₄=SAME AS FIG. 3A-3
R₅=SAME AS FIG. 3A-3
FIG. 3A-4

IF X=O, Y=N
IF X=N, Y=O

R₁=SAME AS FIG. 3A-3
R₄=SAME AS FIG. 3A-3
R₅=SAME AS FIG. 3A-3

IF R₂=H

THEN R₃=

IF R₂=

THEN R₃=H

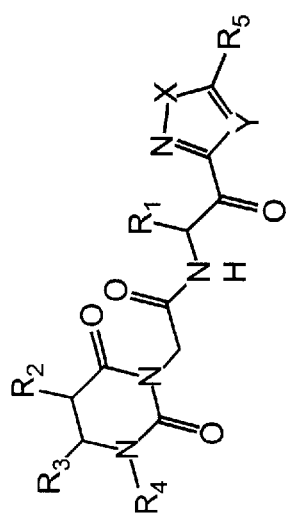
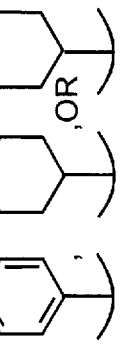
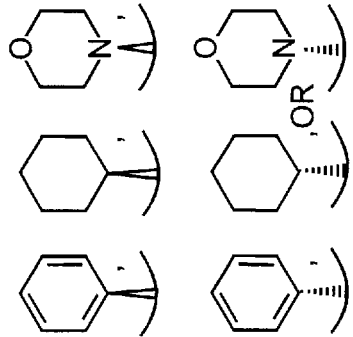
IF X=O, Y=N
IF X=N, Y=O
R₁=SAME AS FIG. 3A-3
R₄=SAME AS FIG. 3A-3
R₅=SAME AS FIG. 3A-3
IF R₂=
THEN R₃=H
IF R₂=H
THEN R₃=
FIG. 3A-6

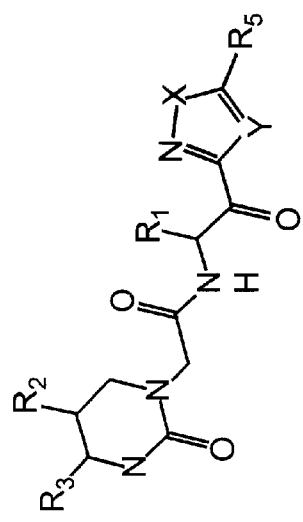
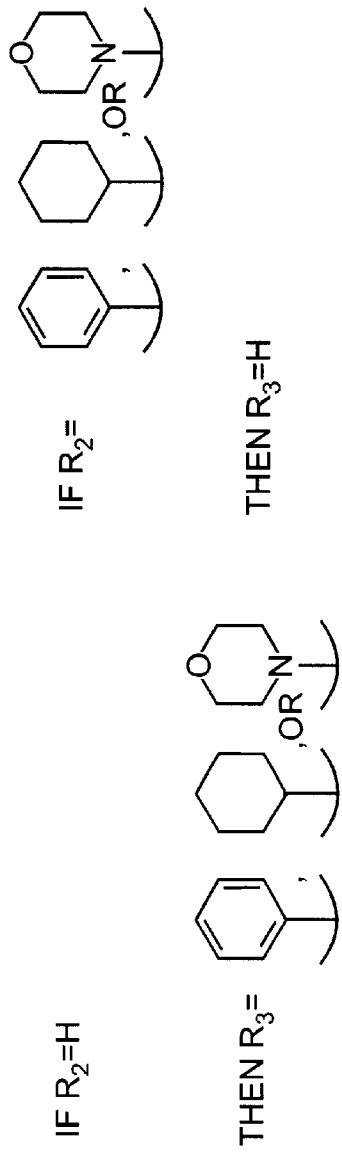
IF X=O, Y=N
IF X=N, Y=O
R₁=SAME AS FIG. 3A-3
R₅=SAME AS FIG. 3A-3
IF R₂=
THEN R₃=H
IF R₂=H
THEN R₃=
FIG. 3A-7

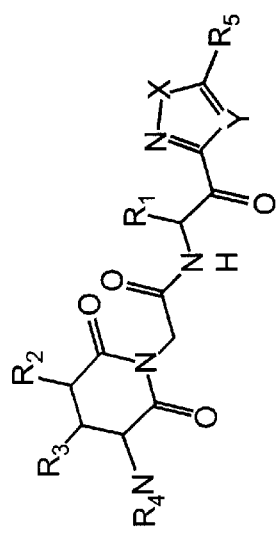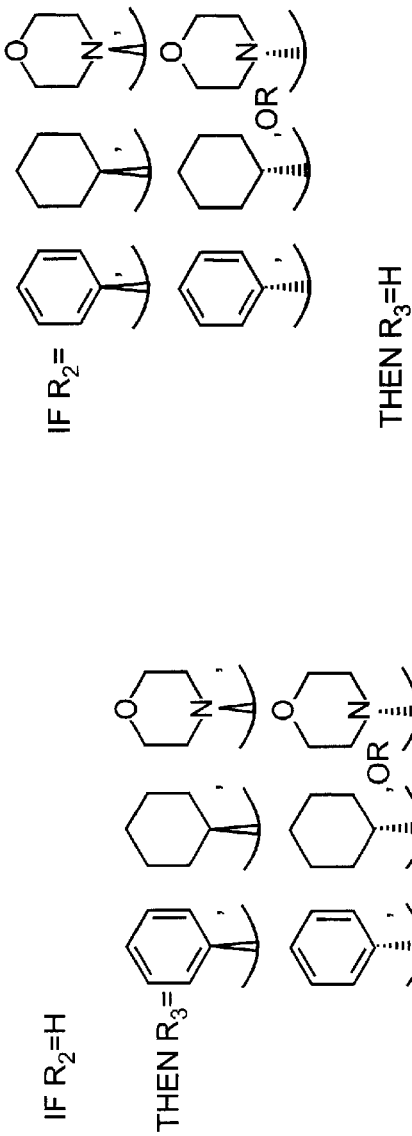
IF X=O, Y=N
IF X=N, Y=O
R₁=SAME AS FIG. 3A-3
R₄=SAME AS FIG. 3A-3
R₅=SAME AS FIG. 3A-3
FIG. 3A-8

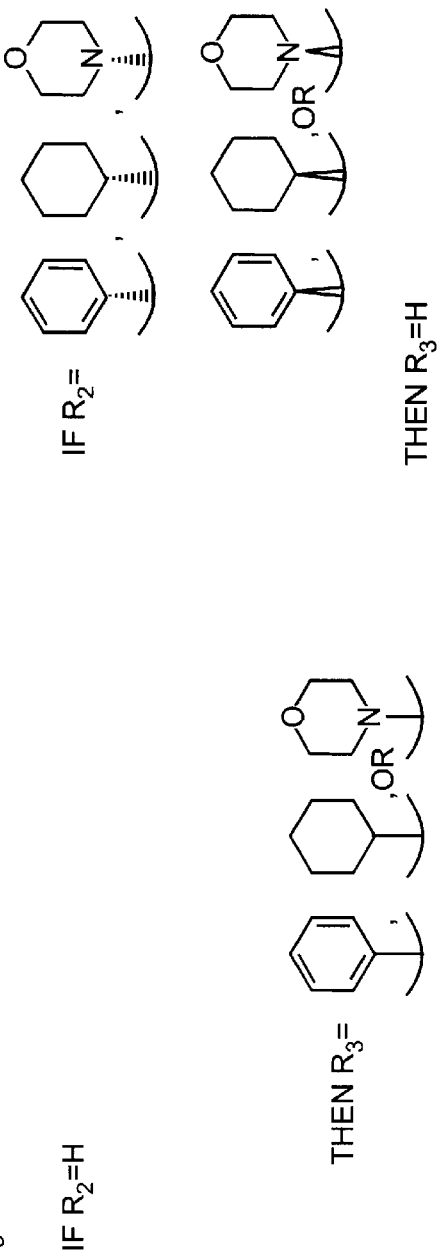
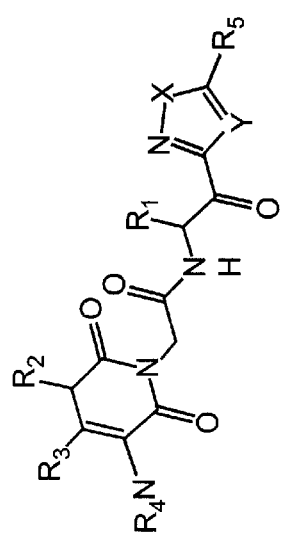
FIG. 3A-9
IF X=O, Y=N
IF X=N, Y=O
$R_1$=SAME AS FIG. 3A-3
$R_4$=SAME AS FIG. 3A-3
$R_5$=SAME AS FIG. 3A-3
IF $R_2$=H
THEN $R_3$=

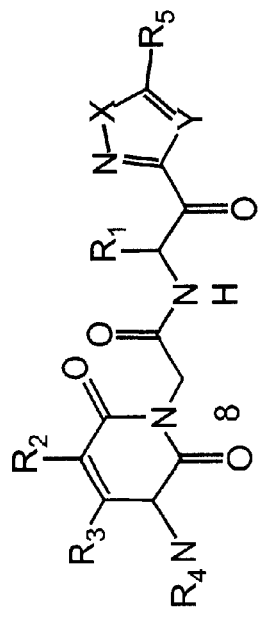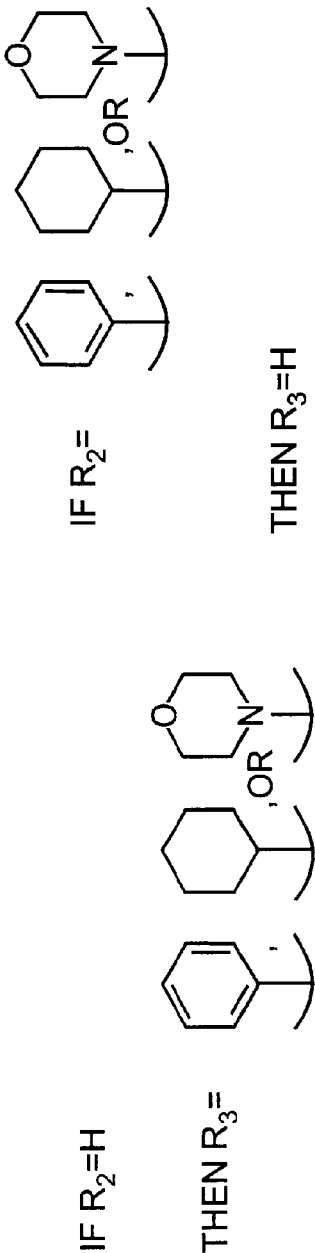
FIG. 3A-10

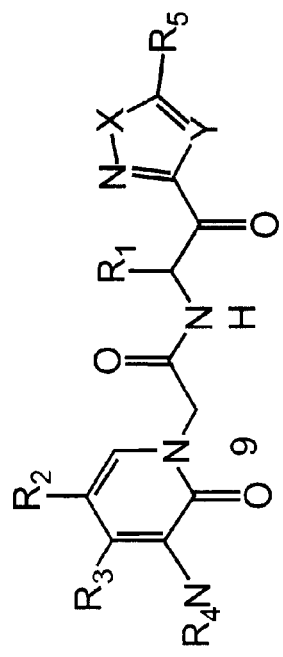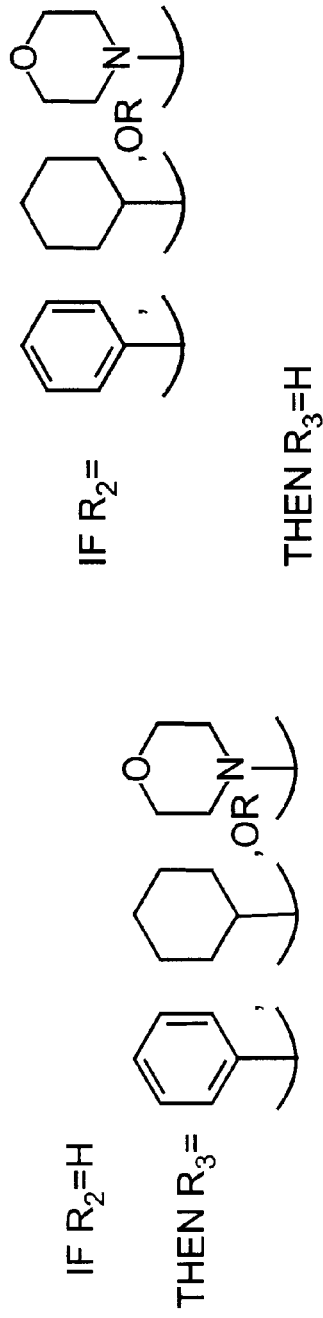
IF X=O, Y=N
IF X=N, Y=O
R₁=SAME AS FIG. 3A-3
R₄N=SAME AS FIG. 3A-3
R₅=SAME AS FIG. 3A-3
FIG. 3A-11

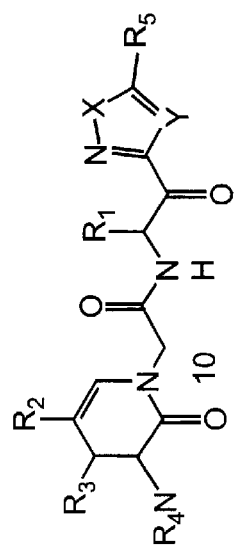
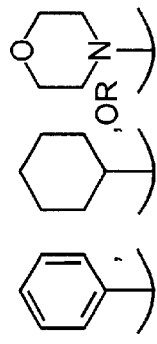
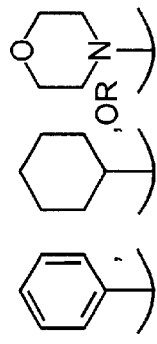
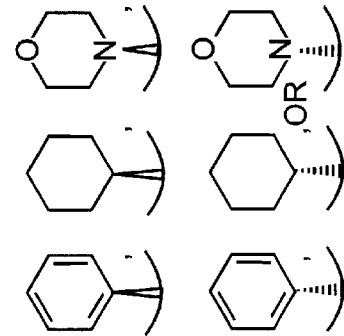
IF X=O, Y=N
IF X=N, Y=O
R₁=SAME AS FIG. 3A-3
R₄=SAME AS FIG. 3A-3
R₅=SAME AS FIG. 3A-3
IF R₂=H
THEN R₃=
IF R₂=
THEN R₃=H
FIG. 3A-12

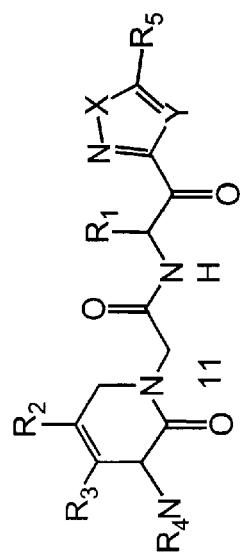
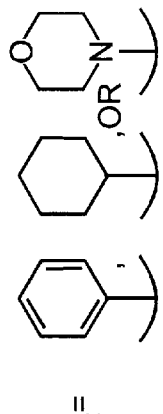
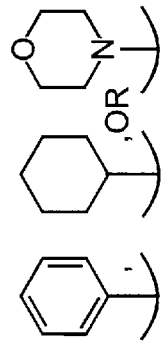
IF X=O, Y=N
IF X=N, Y=O
R₁=SAME AS FIG. 3A-3
R₄=SAME AS FIG. 3A-3
R₅=SAME AS FIG. 3A-3
IF R₂=H
THEN R₃=
IF R₂=
THEN R₃=H
FIG. 3A-13

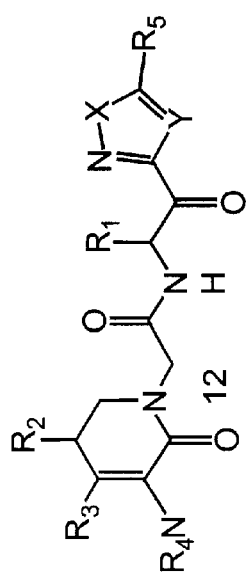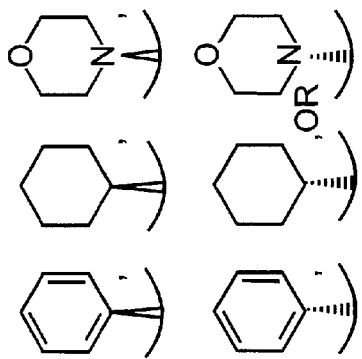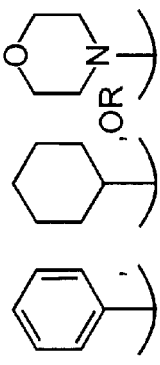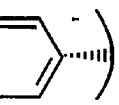
FIG. 3A-14

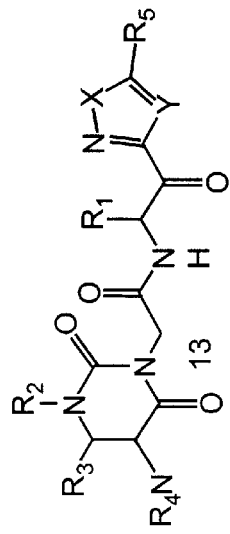
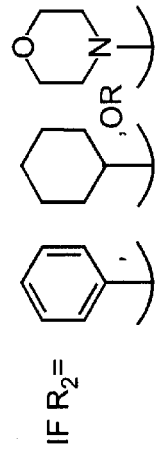
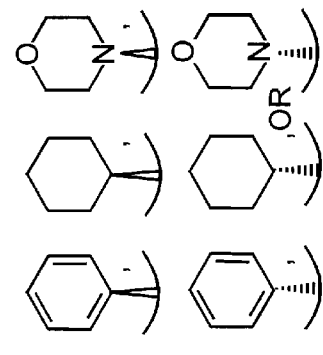
IF X=O, Y=N
IF X=N, Y=O
R$_1$=SAME AS FIG. 3A-3
R$_4$=SAME AS FIG. 3A-3
R$_5$=SAME AS FIG. 3A-3
IF R$_2$=
THEN R$_3$=H
IF R$_2$=H
THEN R$_3$=
FIG. 3A-15

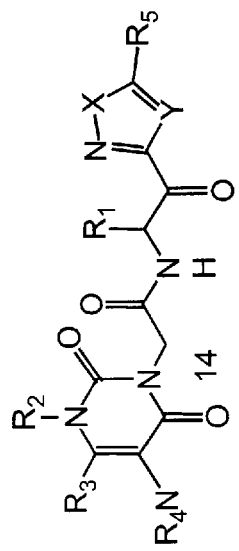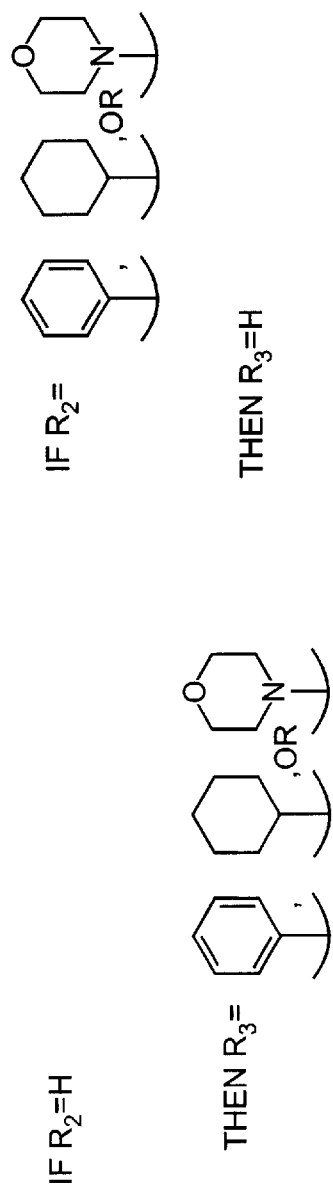
IF X=O, Y=N
IF X=N, Y=O
R₁=SAME AS FIG. 3A-3
R₄=SAME AS FIG. 3A-3
R₅=SAME AS FIG. 3A-3
IF R₂=H
THEN R₃=
FIG. 3A-16

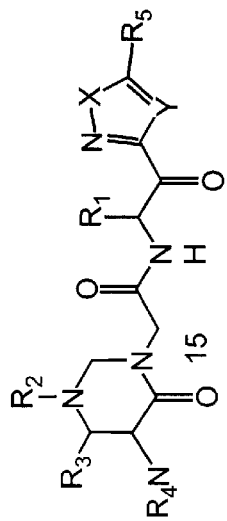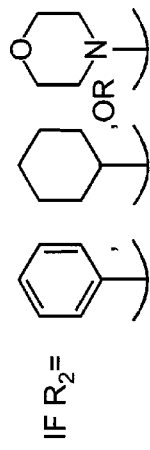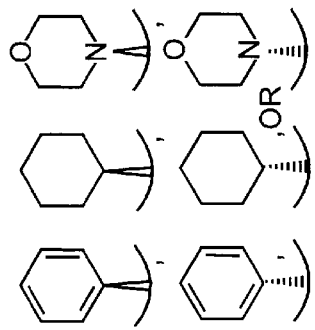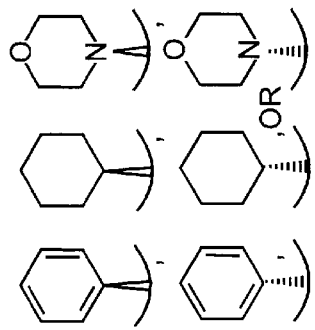
IF R₂=
THEN R₃=H
IF R₂=H
THEN R₃=
IF X=O, Y=N
IF X=N, Y=O
R₁=SAME AS FIG. 3A-3
R₄=SAME AS FIG. 3A-3
R₅=SAME AS FIG. 3A-3
FIG. 3A-17

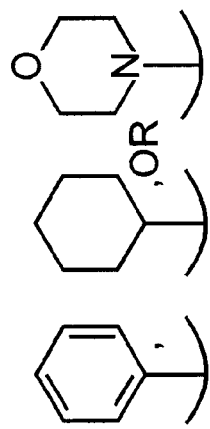
$R_3 =$
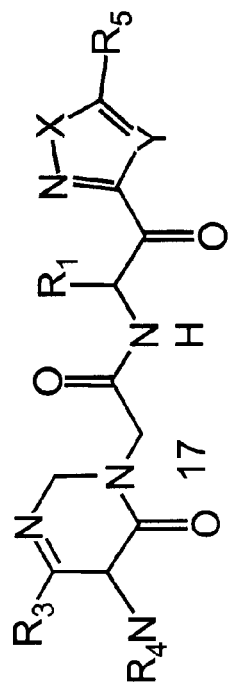
IF X=O, Y=N
IF X=N, Y=O
$R_1$=SAME AS FIG. 3A-3
$R_4$=SAME AS FIG. 3A-3
$R_5$=SAME AS FIG. 3A-3
FIG. 3A-19

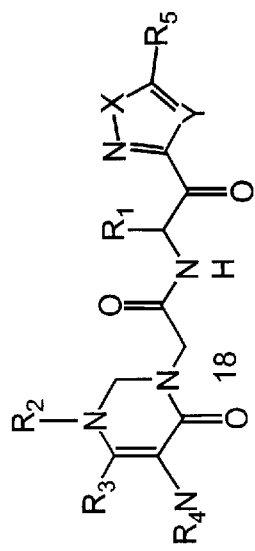
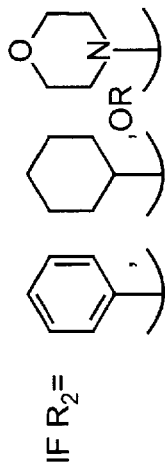
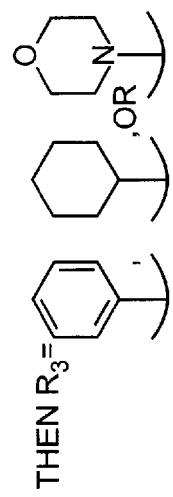
IF X=O, Y=N
IF X=N, Y=O
R$_1$=SAME AS FIG. 3A-3
R$_4$=SAME AS FIG. 3A-3
R$_5$=SAME AS FIG. 3A-3
IF R$_2$=
THEN R$_3$=H
IF R$_2$=H
THEN R$_3$=
FIG. 3A-20

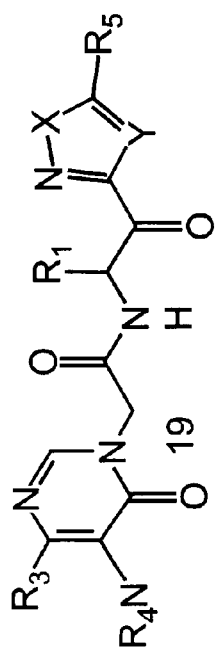
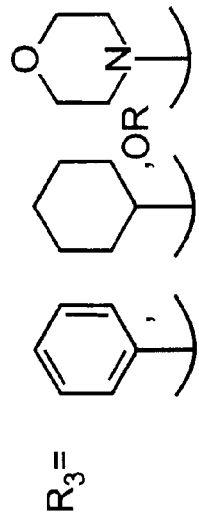
IF X=O, Y=N
IF X=N, Y=O
R₁=SAME AS FIG. 3A-3
R₄=SAME AS FIG. 3A-3
R₅=SAME AS FIG. 3A-3
FIG. 3A-21

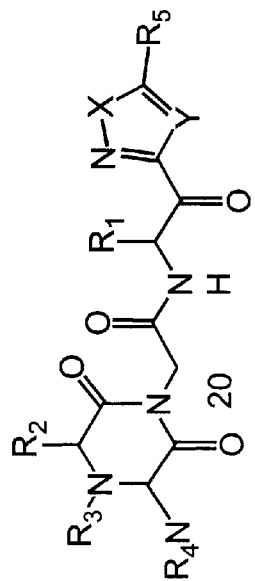
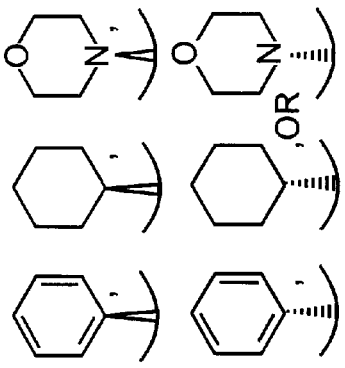
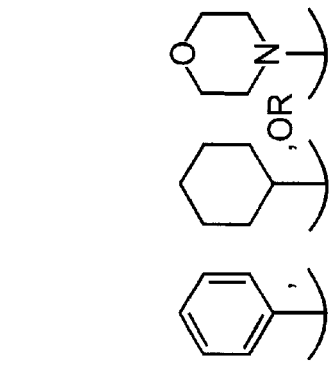
IF X=O, Y=N
IF X=N, Y=O
R₁=SAME AS FIG. 3A-3
R₄=SAME AS FIG. 3A-3
R₅=SAME AS FIG. 3A-3
IF R₂=H
THEN R₃=
IF R₂=
THEN R₃=H
FIG. 3A-22

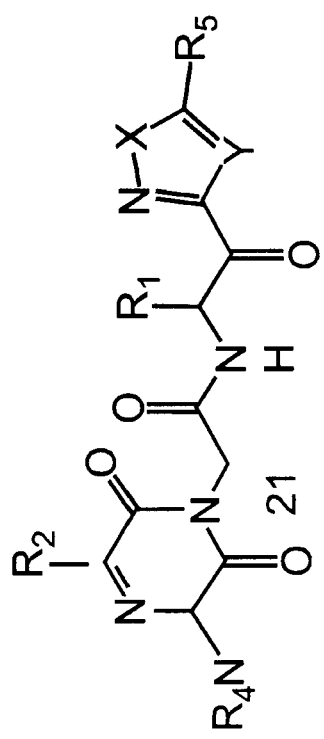
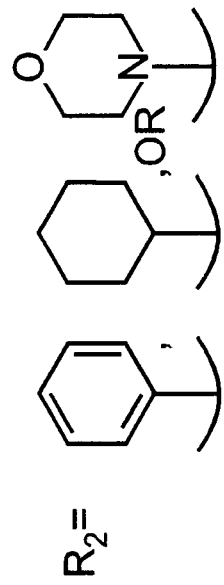
R₂ =
IF X=O, Y=N
IF X=N, Y=O
R₁=SAME AS FIG. 3A-3
R₄=SAME AS FIG. 3A-3
R₅=SAME AS FIG. 3A-3
FIG. 3A-23

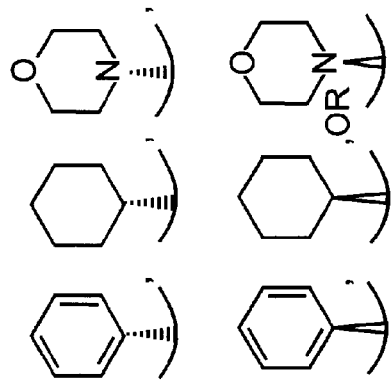
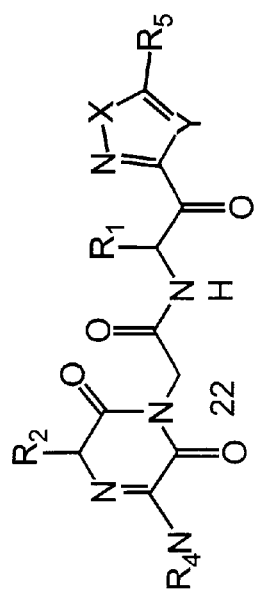
$R_2 =$
IF X=O, Y=N
IF X=N, Y=O
$R_1$=SAME AS FIG. 3A-3
$R_4$=SAME AS FIG. 3A-3
$R_5$=SAME AS FIG. 3A-3
FIG. 3A-24

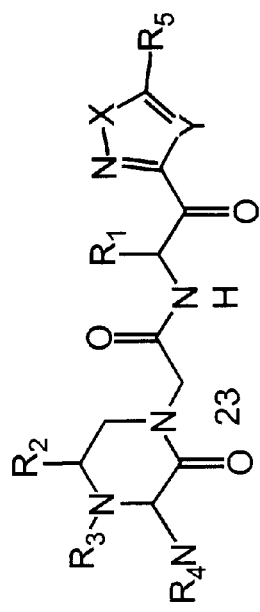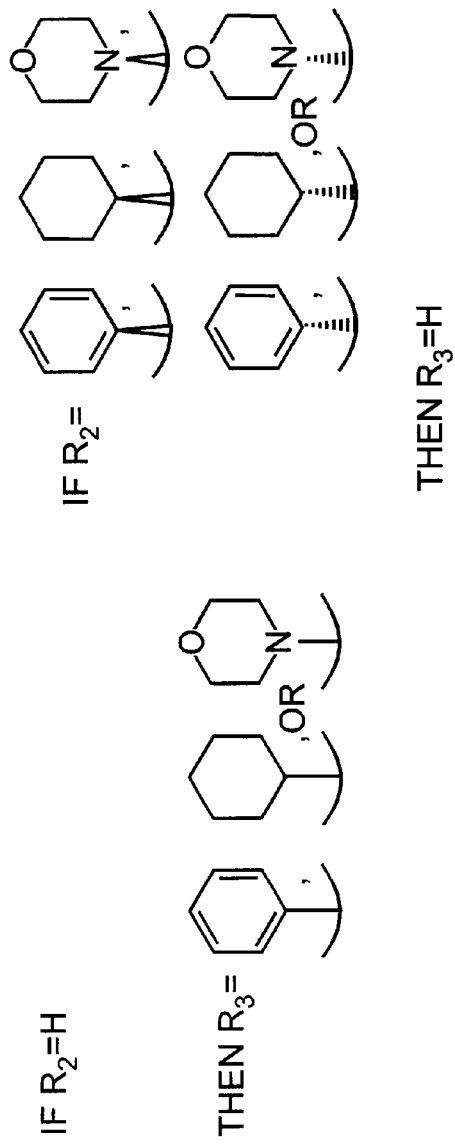
FIG. 3A-25

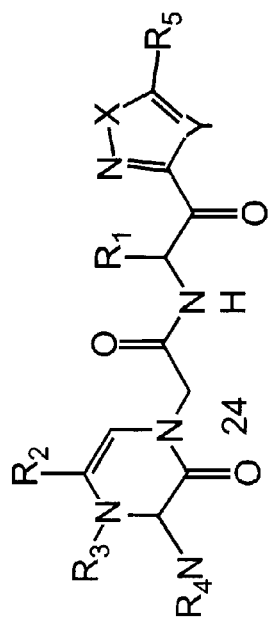
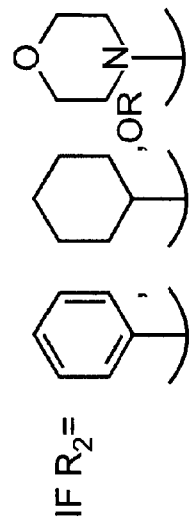
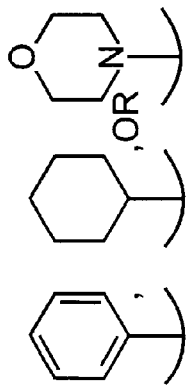
IF X=O, Y=N
IF X=N, Y=O
R₁=SAME AS FIG. 3A-3
R₄=SAME AS FIG. 3A-3
R₅=SAME AS FIG. 3A-3
IF R₂=H
THEN R₃=
IF R₂=
THEN R₃= H
FIG. 3A-26

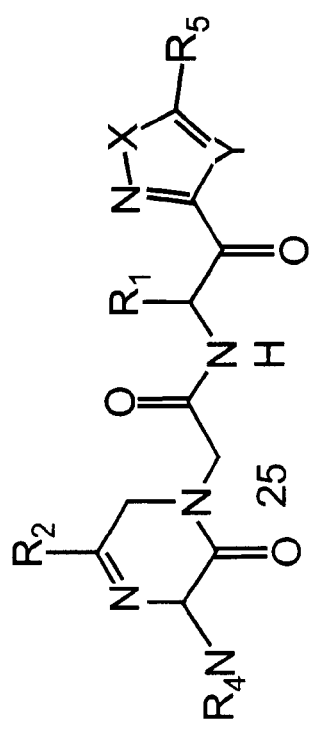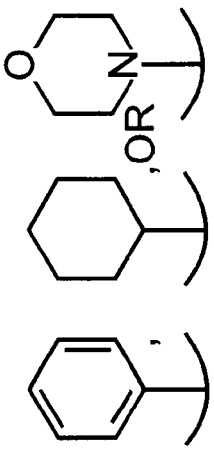
25
IF X=O, Y=N
IF X=N, Y=O
R$_1$=SAME AS FIG. 3A-3
R$_4$=SAME AS FIG. 3A-3
R$_5$=SAME AS FIG. 3A-3
FIG. 3A-27

METHOD AND STRUCTURE FOR INHIBITING ACTIVITY OF SERINE ELASTASES

CROSS REFERENCE

This application gains priority from provisional application No. 60/139,625 filed Jun. 17, 1999 herein incorporated by reference.

BACKGROUND ART

Elastase is a general term that describes a group of protease enzymes that have the ability to degrade elastin. Elastin is the primary extracellular matrix protein that confers elastic qualities to a variety of tissues including the lung, skin and blood vessels. Different proteases from the serine, cysteine and metallo classes have been shown to degrade elastin with varying degrees of activity. In addition to elastin, serine elastases have been shown to degrade or process other proteins with varying relative activities. The serine elastases share the property of preferential cleavage of polypeptides and proteins adjacent to aliphatic amino acid residues, primarily alanine, valine and methionine. These enzymes also cleave, to a variable extent, at sites adjacent to leucine and isoleucine.

Examples of serine elastases include pancreatic elastase (PE), neutrophil elastase (NE), proteinase-3 (PR-3), endogenous vascular elastase (EVE), endothelial cell elastase (ECE)) and at least three other serine elastases including those derived from transformed rat liver epithelial, Schwann cells and human carcinoma cell lines, human skin fibroblasts and human lymphocytes.

Among elastases, the most well studied enzymes are PR-3 and NE. These enzymes are structurally similar but biologically different. Both Proteinase-3 (PR-3) and NE are co-localized in neutrophil primary granules and are co-released from activated human neutrophils. Both enzymes degrade elastin when purified enzyme and substrate are incubated together. However, despite structural similarities, not all endogenous inhibitors of NE inhibit PR-3, for example secretory leukocyte protease inhibitor (SLPI). Furthermore, the biology of NE and PR-3 appears to be significantly different.

NE appears to be primarily responsible for degradation of extracellular matrix (ECM) proteins and other important substrate proteins (immunoglobulins, surfactant apoproteins, etc.). Both NE and PR-3 play roles in the activation of pro-enzymes such as metalloproteinases (MMPs). In contrast, PR-3 rather than NE appears to be particularly well-suited to the processing of pro-cytokines to their active biological forms. The amount of at least two of the more important pro-inflammatory cytokines, produced by monocytic cells, TNF-α and IL-1β has been shown to be differentially enhanced by PR-3 relative to NE. It has also been shown that PR-3, but not NE, can process mature interleukin-8(77) having 77 amino acid residues to a form having approximately 10 fold greater biological activity interleukin-8 (70) having 70 residues.

Inflammatory cell serine elastases (and metalloproteinases) are critical enzymes for directed cell migration of both neutrophils and monocyte/macrophages. Their roles in this context were thought to be limited to the degradation of vascular basement membrane and underlying extracellular matrix proteins. In addition to their activities as matrix degrading enzymes, however, their ability to affect local regulation and amplification of the inflammatory response suggests a broader role in a variety of different disease states.

Some pathological conditions are believed to result at least in part from an imbalance between the elastases and their endogenous inhibitors. Uncontrolled proteolytic degradation by neutrophil elastases, especially NE has been implicated in a number of pathological conditions like pulmonary emphysema, acute respiratory distress syndrome, septic shock, multiple organ failure, rheumatoid arthritis, and cystic fibrosis.

One approach to disease management includes therapeutic intervention with small molecule elastase inhibitors for blocking the activity of particular elastases. For instance, U.S. Pat. No. 5,618,792 to Gyorkos et al., as well as continuation-in-part U.S. Pat. Nos. 5,807,829; 5,861,380; 5,869,455; 5,874,585; and 5,891,852 describe small molecule inhibitors and their method of synthesis that are selective for human neutrophil elastase (NE). These inhibitors of NE were shown to be effective in attenuating elastases-induced lung injury. These patents are hereby incorporated herein by reference.

There has been extensive efforts focused on NE inhibition in a variety of pathological conditions such as pulmonary emphysema, acute respiratory distress syndrome, septic shock, multiple organ failure, rheumatoid arthritis, and cystic fibrosis. This has not been the case for inhibitors of elastases other than neutrophil elastase. Such inhibitors would be useful for enhancing the treatment of the above stated pathologies. Furthermore, elastase inhibitors having specificity for elastases other than NE, such as PR-3, would be useful for treating pathologies such as vascular and inflammatory disorders including restenosis, atherosclerosis and vasculopathy, myocardial infarction, stroke and bronchopulmonary dysplasia.

SUMMARY

Various embodiments of the present invention provide inhibitors and methods of inhibiting the activity of a plurality of serine elastases using a single inhibitor that may have specificity for elastases including neutrophil elastase or have specificity for elastases other than neutrophil elastase.

Accordingly, in a preferred embodiment of the invention, there is provided a serine elastase inhibitor that provides balanced inhibitory activity with respect to a plurality of serine elastases including an agent having a chemical structure including a serine elastase recognition moiety and a warhead moiety. More particularly, the agent may inhibit neutrophil elastase and PR-3. The agent may provide balanced inhibitory activity as a first inhibitory constant for NE and a second inhibitory constant for PR-3 that may differ by no more than two orders of magnitude, more specifically by fifty fold, and preferably by no more than one order of magnitude.

In another embodiment, one of the serine elastase recognition moiety (SERM) and the warhead moiety (WHM) contains a carbonyl group, the SERM further containing a first submoiety, the warhead further containing a heterocycle warhead submoiety, such that a carbonyl carbon of the carbonyl group directly attaches to a carbon of the heterocycle submoiety, in addition to the first submoiety. The SERM may contain one of a plurality of first submoieties. In a preferred embodiment, a method is provided that includes administering to an environment containing serine elastase, an effective amount of a serine elastase inhibitor, the agent having a chemical structure including a serine elastase recognition moiety and a warhead moiety, the agent being provided in a pharmaceutically acceptable carrier, the serine elastase inhibitor having balanced inhibitory activity with respect to a plurality of serine elastases. The serine elastases include neutrophil elastase and PR-3.

In a preferred embodiment of the invention, a compound is provided with the formula:

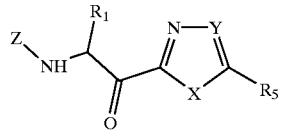

wherein Z is selected from the group consisting of: any of the structures listed in FIG. 5 or any derivatives or analogs thereof.

$R_1$ is selected from the group consisting of methyl (—$CH_3$), ethyl (—$CH_2CH_3$), propyl (—$CH_2CH_2CH_3$), butyl (—$CH_2CH_2CH_2CH_3$), (—$CH_2CH_2$—S—$CH_3$), (—$CH_2$—S—$CH_3$), (—$CH_2CH_2$—O—$CH_3$), (—$CH_2$—O—$CH_3$), and (—$CH_2$—O—$CH_2CH_3$) corresponding to the side chains of alanine, aminobutyric acid, norvaline, norleucine, methionine and homomethionine.

$R_2$ is selected from the group of phenyl, cyclohexyl, morpholino, H;
$R_3$ is selected from the group of phenyl, cyclohexyl, morpholino, H;
$R_4$ is H or,

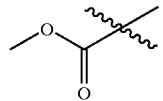

$R_5$ is selected from alkyl, alkenyl, haloalkyl, haloalkenyl, alkynyl being linear or branched; a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamido, arylcarboxamido, alkylthio, or haloalkylthio groups being linear or branched; a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamido, arylcarboxamido, alkylthio or haloalkylthio groups being linear or branched; and X and Y are independently O, S or N wherein N is optionally substituted with alkyl, alkenyl, alkynyl being linear or branched; a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamido, arylcarboxamido, alkylthio, or haloalkylthio groups being linear or branched; a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamido, arylcarboxamido, alkylthio or haloalkylthio groups being linear or branched, provided at least one of X or Y is N; and provided that where both X and Y are N, only one of X or Y is substituted; $R_1$, $R_2$, $R_3$, $R_4$, $R_5$ being further selected from any of the structures described in FIG. 3.

In a preferred embodiment, a pharmaceutical formulation is provided for treating an elastase induced pathology, that includes an effective dose of a compound such as described above.

In a further embodiment of the invention, a method is provided for inhibiting proteinase-3 or neutrophil elastase, or proteinase-3 and neutrophil elastase, in which a compound according to any listed above is administered in an effective dose in a pharmaceutically acceptable formulation.

Additional embodiments of the invention include providing balanced inhibitory activity for a plurality of elastases that further include endovascular (EVE), or endothelial cell (ECE).

DETAILED DESCRIPTION OF SPECIFIC EMBODIMENTS

The present invention is directed to novel inhibitors and methods for inhibiting serine elastases. These compounds and methods achieve a novel approach to enzyme inhibition, namely balanced inhibition of a plurality of serine elastases. Balanced inhibition of a plurality of elastases offers a novel approach to therapeutic treatment of diseases that involve abnormal activities of a plurality of elastases resulting in pathological changes such as occur in inflammatory and vascular conditions. These pathological changes are not limited to the breakdown of elastin but may include the processing of other proteins by serine elastases which in turn results in adverse effects. The opportunity of targeting a plurality of enzymes using a single inhibitor offers therapeutic advantages over administering multiple therapeutic agents where each agent has a single specificity for an individual target enzyme.

Figure 1:
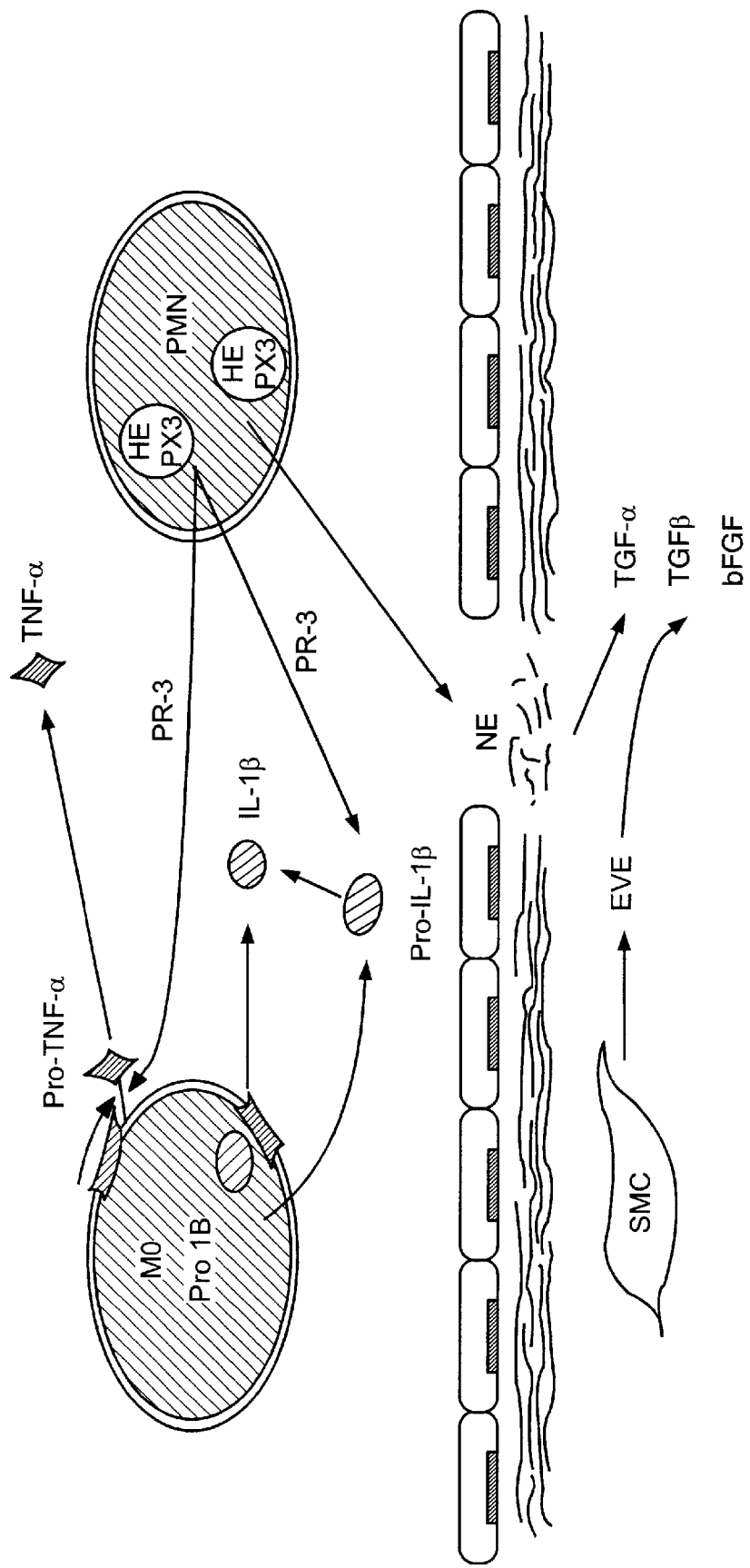
FIG. 1 illustrates the involvement of serine elastases in inflammatory and vascular diseases.

Multiple serine elastases may be involved in a single pathological condition. FIG. 1 shows how interactions between the serine elastases that are derived from multiple cell types arise in the context of inflammatory vascular conditions. Under these conditions, neutrophil elastase (NE) and endogenous vascular elastase can degrade vascular extracellular matrix, releasing latent or matrix-bound growth factors that can then go on to interact with vascular cells such as smooth muscle cells (SMC) and endothelial cells (EC). NE and endothelial cell elastase can interact with EC to stimulate release of platelet activating factor, which can both attract and stimulate inflammatory cells such as neutrophils (polymorphonuclear leukocytes) and macrophages/monocytes. Proteinase-3 (PR-3), then, can augment the release of monocyte derived cytokines such as tumor necrosis factor α and interleukin-1β which can further amplify the inflammatory process. (Cheronis and Rabinovitch, Handbook of Experimental Pharmacology vol. 140. Proteases as Targets for Therapy. Ch 14, ed. K. von der Helm, B. D. Korant, J. C. Cheronis. Pub. Springer Verlag Berlin 2000).

The following terms are defined here and in the claims as follows:

"Serine elastase recognition moiety" (SERM) is a moiety of the chemical structure of an inhibiting agent which is identified by and associates with a corresponding moiety of a serine elastase enzyme thereby facilitating inhibitor-enzyme coupling. (FIG. 2) Such coupling may be reversible or irreversible. SERM submoieties including $P_i$, represent specific chemical substructures thought to identify and associate with specific substrate binding subsites, $S_j$, of an elastase. (FIG. 2) The number of inhibiting agent submoieties, i, may differ from the number, j, of elastase submoieties. Typically, i may range from 1–5, while j is usually 3 or more. In most cases, both $P_i$ and $S_j$ structurally depend from or are based upon a first submoiety, where the first submoiety is defined here and in the claims as any of an amino acid, peptide or peptidomimetic submoiety or any analog or derivative thereof. A first submoiety (which may be denoted as $P_1$) may apply herein and within the context of the accompanying FIGS., to X or to any other component of the SERM or to the SERM as a whole. A carbonyl group is frequently present in the inhibitor structure at or near the SERM/warhead bond. The carbonyl group may, for purposes described in the disclosure be defined as a submoiety of the SERM or of the warhead.

"Warhead" moiety (WHM) is a moiety of an inhibitor which interferes, either reversibly or irreversibly, with the reaction of an enzyme with a substrate. Warheads may, for example, form covalent bonds with the enzyme, may create stable transition states, or be reversible or irreversible alkylating agents. "Heterocycle warhead" submoiety (HWSM) is a warhead submoiety most directly bonded to the SERM of the structure (usually at or near a characteristic carbonyl group). It is generally limited in extent to a heterocyclic ring with its associated heteroatoms. "Substitution warhead" submoiety (SWSM) is a warhead submoiety, usually a chemical group, bonded to a position on the heterocyclic ring other than the positions to which are bonded a carbon atom, a heteroatom, or the SERM (or associated carbonyl group).

"Inhibitor constant" is defined as a measured quantity which is proportional to the concentration of inhibitor multiplied by the concentration of enzyme (elastase) divided by the concentration of coupled inhibitor enzyme (typically denoted $K_i$).

"Balanced inhibitory activity" with respect to a plurality of elastases is defined as such inhibitor constants measured with respect to each elastase differing by no more than two orders of magnitude.

"Pharmaceutically acceptable carrier" includes any and all solvents, dispersion media, coatings, antimicrobials (e.g., antibacterial or antifungal agents), isotonic agents, absorption delaying agents, that are physiologically compatible.

Cbz is a defined shorthand notation for a benzyloxycarbonyl group.

Abu is a defined shorthand notation for aminobutyric acid.

In order to treat the diseases involving synergistic or additive elastase activity, parallel or sequential elastase activity or excess redundant activities between elastases, it is desirable or even necessary to inhibit a plurality of elastases rather than to inhibit any single elastase. In particular, inhibition of both PR-3 and NE have particular utility because of the important role of these enzymes in pathology (FIG. 1). Although it is possible to target the elastases individually using a combination of inhibitors specific for NE and for PR-3 respectively, a balanced inhibition of a plurality of serine elastases with a single inhibitor is preferred. The benefits of administration of a single agent in place of multiple agents include reduced cost of development and improved benefit for the patient. Benefits also include avoiding drug interactions that may prove harmful to the patient. In addition, the measurement of efficacy of a single agent may be assessed more readily than can a cocktail of agents.

An important feature of the preferred embodiments of the invention is the "balanced inhibitory activity." This activity is possible because the class of elastases share common basic features. The elastases have similar substrate specificity, namely an ability to cleave elastin. Moreover, elastases such as NE and PR-3, are structurally similar, especially in their active site region, and show similarities as well as differences in their ability to bind substrate more particularly low-molecular-weight peptide substrates. The similar active site regions of the various elastases provide a target for the same kind of "SERM_moiety" provided that the design of the SERM moiety takes into account the differing properties of binding sites for different elastases.

As a consequence of inhibiting a plurality of serine elastases, a "balanced inhibitor" may be more effective in treating a pathological condition involving NE than single enzyme inhibitors that are specific for neutrophil elastase and currently used for example, in the treatment of diseases such as cystic fibrosis, acute respiratory-distress syndrome. Furthermore, "balanced" inhibitors may be therapeutically effective for groups of diseases not previously treated with NE inhibitors. The group of diseases include, but not limited to, restenosis, atherosclerosis and vasculopathy, myocardial infarction, stroke and bronchopulmonary dysplasia.

Although the prior art describes many compounds that have been found to be effective in inhibiting the activity of NE, the inhibitory activities of these compounds are also highly specific. While these compounds have significant inhibitory activity against NE, most of the compounds show almost no inhibitory activity against other proteases, including NE's close family member, PR-3.

Figure 2:
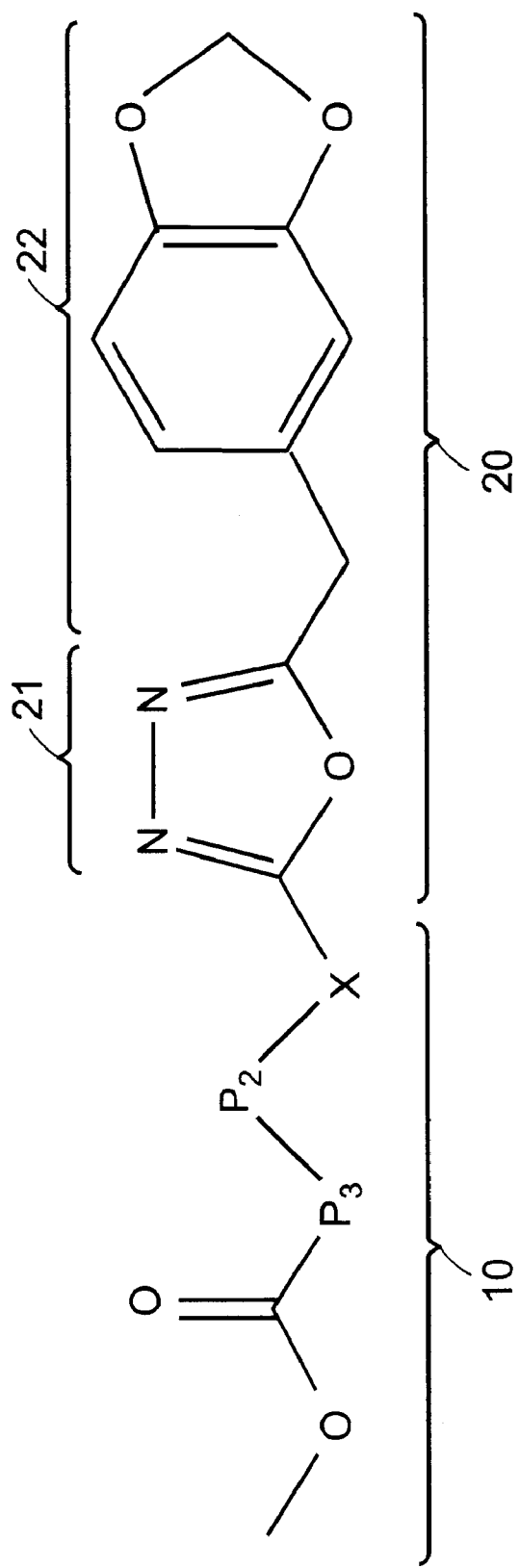
FIG. 2 illustrates a chemical structure for an inhibitor capable of providing balanced inhibitory activity delineating SERM 10 and WHM 20.

We have developed novel compounds to achieve balanced inhibitory activity. Although not wishing to be limited by theory, we propose that the shape of the binding pockets as determined using crystallography plays a role in determining whether an inhibitor will have balanced activity for a plurality of elastases. The comparison of the crystal structures of NE and PR-3 shows that NE has a large binding pocket for substrates or inhibitors, whereas PR-3 has a long and narrow binding pocket. Valine or leucine adjacent to the warhead have been shown in the prior art to play a key role in the specificity of an inhibitor for NE. This appears to be because the large binding pocket of NE can accommodate valine or leucine, which have branched side chain moieties that fit well into the binding pocket of NE but not into the binding pocket of PR-3. Replacing the valine or leucine with a residue with a linear side chain produces a new compound that fits into PR-3, while the new side chain can still be accommodated by the large binding pocket of NE. In this way, a "balanced inhibitory activity" against both NE and PR-3 results. The valine or leucine can be replaced with any amino acid, peptide, peptidomimetic, or derivatives or analogs thereof, but preferably with those having aliphatic side chains, such as alanine, aminobutyric acid, norvaline, norleucine, methionine or homomethionine. The first moiety more particularly X in FIG. 2 provides a context for positioning the R group or side chain of the peptide or peptidomimetic into the binding pocket that provides specificity for the inhibitor, the specificity being a significant factor in the observed balanced inhibitory activity.

The compounds in which valine is substituted with an aliphatic aminoacid, peptide or peptidomimetic are synthesized according to the methods and protocols disclosed in U.S. Pat. No. 5,618,792 to Gyorkos et al., as well as continuation-in-part U.S. Pat. Nos. 5,807,829; 5,861,380; 5,869,455; 5,874,585; and 5,891,852 herein incorporated by reference. Those compounds were then tested for their inhibitory activities against both NE and PR-3 and other proteases, including porcine pancreatic elastase (PPE), chymotrypsin (CHYM), cathepsin-G (Cat-G), and trypsin, cathepsin-L (Cat-L), matrix metalloproteinase-8 (MMP-8), and thermolysin. According to the test results, the "balanced" inhibitors are selected out for further pharmaceutical development for treatment of the inflammatory and vascular diseases including, but not limited to, restenosis, atherosclerosis, transplant vasculopathy, myocardial infarction, stroke, and bronchopulmonary dysplasia.

The screening assay may also be used to identify novel non-"balanced" inhibitors such as a compound with high inhibitory activity against PR-3 but no inhibitory activity against any other proteases, including NE. A specific PR-3 inhibitor can be used alone or in combination with specific NE inhibitors for targeting specific pathologic conditions that for some reason are not amenable to inhibition by "balanced" inhibitors.

The "warhead moiety" of the "balanced" inhibitor can be any chemical group that is capable of interfering on the active site regions of serine proteases. For example, although 1–3,4 oxadiazol may be coupled to the SERM, other warheads known in the art may also be used including: (1) non-oxadiazole heterocycles, more specifically benzoxazoles or substituted benzoxazoles; (2) perfluorinated alkyl ketones, including trifluoromethyl ketones or pentafluoroethylketones;(3) halomethyl ketones; (4) boronic acids (5) aldehydes; (6) di-ketones, alpha keto acids and alpha keto esters and (7) active esters.

Figure 3A:
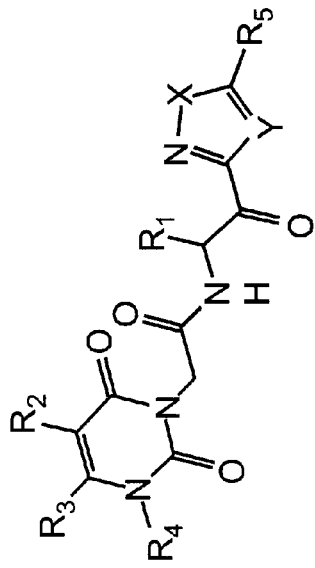
FIG. 3 illustrates examples of alternative $P_1$ configurations and warhead moiety combinations including alternative structures for the subrecognition moiety.
Figure 3:
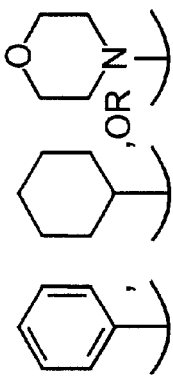
Figure 4:
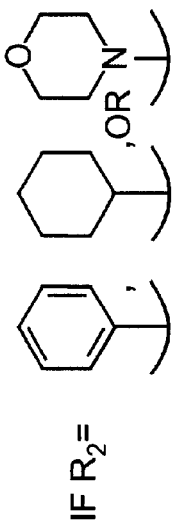
FIG. 4 illustrates substrate and elastase subsite binding. $P_{1-n}$ are amino acids of the substrate. $S_{1-4}$ are subsites of the overall substrate binding site of the protease (elastase).

Heterocycle warheads may also be used, including:

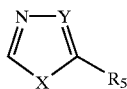

where $R_5$ may include alkyl, alkenyl, haloalkyl, haloalkenyl, alkynyl being linear or branched; a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamido, arylcarboxamido, alkylthio, or haloalkylthio groups being linear or branched; a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamido, arylcarboxamido, alkylthio or haloalkylthio groups being linear or branched; and X and Y are independently O, S or N wherein N is optionally substituted with alkyl, alkenyl, alkynyl being linear or branched; a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamido, arylcarboxamido, alkylthio, or haloalkylthio groups being linear or branched; a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamido, arylcarboxamido, alkylthio or haloalkylthio groups being linear or branched, provided at least one of X or Y is N; and provided that where both X and Y are N, only one of X or Y is substituted including $R_5$ as listed in FIG. 3.

Thus, with each "balanced" inhibitor or specific PR-3 inhibitor, a whole family of "balanced" inhibitors or PR-3 inhibitors can be developed with different "warhead moiety" capable of interfering all serine proteases.

The residue in the position of valine is not the only moiety within the "serine elastase recognition" moiety of inhibitors to play a key role in determining the specificity of the inhibitor. The sub-recognition-moiety linked to N-terminal of the residue also contributes to the determination of the specificity of an inhibitor.

According to the binding pocket structures of the targeted elastases, e.g., NE and PR-3, the sub-recognition-moiety can be modified to make the "balanced" inhibitor more suited, or at least equivalently suited for all the targeted elastases, and thereby produce new "balanced" inhibitors. The sub-recognition moiety can include but is not limited to any of the structures listed in FIG. 5 including derivatives and analogs thereof. $R_2$, $R_3$ is selected from the group of phenyl, cyclohexyl, morpholino, and H; $R_4$ is H or

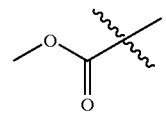

With the above described novel sub-recognition-moieties, new compounds may be produced and then tested for inhibitory activities against various elastases, following the same procedures described above. According to the test results, novel compounds having improved or equivalent "balanced inhibitory activity," or specific inhibitory activity against PR-3 have been identified. As discussed above, all those different inhibitors may be utilized for the treatment of inflammatory and vascular diseases.

Furthermore, the molecular design principles described above can also be used in general to develop compounds with "balanced inhibitory activity" against any plurality of various elastases or proteases, e.g., NE, PR-3, and EVE, as long as such "balanced" inhibitors are needed in treatment of the related diseases.

Referring to FIG. 2, a substituted heterocyclic compound structure includes SERM 10, warhead moiety 20, HWSM 21, and SWSM 22. SERM 10 is shown as including chemical groups $P_1$, $P_2$ and $P_3$ (FIG. 4) which, without being bound to a particular theory, are believed to affect the ability of the substrate to inhibit the activity of particular elastase enzymes. Well known synthetic substrates of NE have an alanine, a proline and a valine in $P_3$, $P_2$ and $P_1$ positions, respectively. Substitutions in all three positions can nevertheless result in a molecule that is effective in inhibiting the activity of, for example, NE, PR-3, ECE, and EVE. Improvements in inhibitory power appear coupled with the properties of $P_1$ (of SERM 10), with respect to size, shape, and bonding characteristics, for mimicking analogous chemical submoieties $S_j$ of a targeted enzyme. Just as a substrate, with submoieties usually denoted by $P_1$, can target a particular elastase enzyme and provide a good physicochemical fit with the enzyme, an effective inhibitor will also provide such a fit and compete for binding with the enzyme. Thus, amino, peptide or peptidomimetic/carbonyl containing submoieties are preferred for $P_1$ (X in FIG. 1 is $P_1$ in FIG. 4), $P_2$ and $P_3$ (P is not limited to 3 although shown in FIG. 2 to be equal to 3). Alanine and proline have been used as $P_2$ and $P_3$, respectively, in a number of the examples described below (FIG. 3, 1–6)

Class A HWSM 21 of warhead moiety 20 is defined by the formula:

wherein, the circle within the ring denoting that the ring is unsaturated, and wherein e and f are independently O, S or N wherein N is optionally substituted with alkyl, alkenyl, alkynyl being linear or branched; a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamido, arylcarboxamido, alkylthio, or haloalkylthio groups being linear or branched; a heteroaryl, heteroarylalkyl or heteroarylalkenyl, and wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamido, arylcarboxamido, alkylthio or haloalkylthio groups being linear or branched, provided at least one of e or f is N; and provided that where both e and f are N, only one of e or f is substituted.

Many of the structure examples (including that of FIG. 2) below include a preferred HWSM 21, namely 1–3,4 oxadiazole, with formula:

HWSM 21 of warhead moiety 20 is not limited to the aforementioned structure defined to be Class A. In addition, the following list discloses other suitable classes of HWSM 21 for warhead moiety 20: a non-oxidiazole heterocycle including benzoxyzole and substituted benzoxazole; perfluorinated alkylketone including trifluoromethyl ketone and pentafluoroethyl ketone; halomethyl ketone, boronic acid, aldehyde, di-ketone, alpha keto acid, alpha keto ester; and active ester.

In vitro toxicity levels for the warhead moiety 20 may limit the number of appropriate heterocycle warhead submoieties 21 for use with a pharmaceutically acceptable carrier.

The SWSM (substitution warhead submoiety) 22 of FIG. 2 is herein defined as Class I. The chemical structure of a Class I SWSM 22 is methylene dioxyphenyl.

Variations in SERM 10 of elastase inhibitors permit changes in specificity that permit balanced inhibition of elastases in addition to NE inhibition. Various permutations of particular submoieties such as $P_I$ (FIG. 4) provide modulation of inhibitory activity against various elastases including, but not limited to PR-3, ECE, and EVE. FIG. 3 describes numerous variations in the particular submoiety, X ($P_1$), of the SERM 10 described in FIG. 2 which will target and inhibit elastase enzymes. For the first twelve variations (FIGS. 3(a) and (b)), alanine or valine is used as $P_3$ and proline is used as $P_2$. The $P_1$, to keep consistent nomenclature, are amino acid residues, peptides, peptidomimetics or their analogs or derivatives as described above. $R_1$ refers to aliphatic side chains of X.

Each of the structures derived from the variations (FIG. 3) in SERM 10 will have different inhibitor constants (sometimes referred to as $K_I$) for different elastase enzymes. A focus upon proposed use of a structure for the inhibition of, for example, both NE and PR-3 should include consideration of the relative constants for the structure for both enzymes. Ideally, the constant for NE would be identical to the constant for PR-3 so that one reaction would not dominate. In real world terms, a difference of no more than two orders of magnitude in inhibitory constants would be acceptable; as little as a five-fold difference much preferred. For example, use of leucine within SERM 10 at $P_1$ is preferred for selective NE inhibition; alanine for example would be preferred for PR-3 inhibition. Use of another group or groups at $P_{2/3}$ may be optimal for targeting both elastases at similar inhibitory levels. Referring now to variations described in FIG. 3 both SERM 10 and the warhead 20 moieties are disclosed and illustrated. Class A HWSM 21 and Class II SWSM 22, having SWSM 22 structure α-dimethylbenzyl methylene dioxybenzyl, variations are included. Class A HWSM 21 and Class III SWSM 22, having SWSM 22 structure tertiary butyl are also included.

EXAMPLES

Example 1. The Synthesis and Characterization of Elastase Inhibitors

Synthesis of peptidic compounds follows the description and procedure of U.S. Pat. No. 5,618,792 to Gyorkos et al., as well as continuation-in-part U.S. Pat. Nos. 5,807,829; 5,861,380; 5,869,455; 5,874,585; and 5,891,852. IR spectra were taken on a Perkin-Elmer 1600 Series FTIR spectrometer. NMR spectra were recorded on a Varian Gemini 300 operating at 300 MHZ for $^1H$ and 75 MHZ for $^{13}C$ or a Bruker 400 spectrometer operating at 400 MHZ for $^1H$ and 100 MHZ for $^{13}C$. HPLC analysis were performed on a Hewlett-Packcard 1050 instrument equipped with a YMC-pack ODS-AQ 5-mm 120 A° analytical column, with acetonitrile/water containing 0.05% trifluoroacetic acid as eluting solvent. Preparative HPLC was performed on a Waters Delta Prep3000 system equipped with a YMC-pack ODS-AQ S-10P 120 A° column using acetonitrile/water containing 0.05% trifluoroacetic acid as eluting solvent. Purification by column chromatography was done on silica (63–200 mesh). Mass spectra were performed by M-Scan, Inc., using fast atom bombardment analysis on a VG analytical ZAB 2-SE high-field-mass spectrometer Example 2: The Measurement of Inhibitory Activities of Compounds Against Various Proteases.

NE. Reactions were performed in 0.05 M sodium phosphate, 0.1 M NaCl, 0.005% Triton X-100, 5% DMSO, pH 7.6 ($K_i$ can also be measured in Hepes buffer). MeOSuc-Lys(2-picolinoyl)-Ala-Pro-Val-pNA and MeOSu-(2-picolinoyl)-Ala-Ala-Val-pNA (pNA is para-nitroaniline)

served as substrates, usually at a 0.5 mM concentration. Final enzyme concentrations were in the range of 2–20 nM. EI complex dissociation experiments with strong inhibitors required especially low final enzyme concentrations. PPE, CHYM, Cat-G, and trypsin. Reaction were performed in 0.1 M Hepes, 0.1 M NaCl, 10 mM CaCl$_2$, 0.005% Triton X-100, 5% DMSO, pH 7.6, using Suc-Ala-Ala-Pro-Leu-pNA (para-nitroaniline), Suc-Ala-Ala-Pro-Leu-pNA, Suc-Ala-Ala-Pro-Phe-pNA, and Bz-Arg-pNA as substrates (0.5 mM), respectively.

PR-3: Reactions were performed in the Herpes buffer described above. Substrate was Boc-Ala-ONp (0.63 mM). Release of p-nitrophenol was monitored at 400–410 nM. Enzyme reaction rates were corrected for spontaneous hydrolysis of the substrate.

Cat-L: The enzyme was activated as described in Methods Enzymol. 80, 535–561(1981), and Biochem. J. 264, 475–481 (1989), and assayed in 0.34 M sodium acetate, 2.5 mM DTT, 1 mM EDTA, 0.1% Brij 35, pH 5.5. Fluorogenic substrate was Z-Phe-Arg-AMC.

MMP-8: Reactions were performed in 0.05M Tris, 0.15 M NaCl, 5 mM CaCl2, 0.02% bovine serum albumin pH 7.4. Internally quanched 7-methoxycoumarin-4-acetyl-Pro-Leu-Gly-b-(2,4-dinitrophenylamino)Ala-Ala-Arg amide was used as a fluorogenic substrate.

Thermolysin: Inhibition of enzyme activity was measured spectrophotometrically using 3-(2-furylacryloyl)-Gly-Leu-CONH$_2$ as a substrate.

Example 3: Stability Studies

Stability of compounds in human plasma was determined as follows. Human plasma was obtained from two male and two female volunteers and previously stored frozen. Plasma was "spiked" with the compounds to a concentration of 0.025 nM. Samples were incubated 0, 3, and 6 hours at 37.degree. At each point protein was precipitated by addition of acetonitrile made 0.1 N HCl (3 parts of solution per part of sample). Samples were subjected to centrifugation (15–20 min at 14,000 rpm) and analyzed (200 mL) with reverse-phase HPLC using a 18–90% acetonitrile gradient in 0.1% TFA.

Example 4: $K_i$ Values

The $K_i^{app}$ values were calculated by a non-linear regression analysis program (ENZFITTER, Elsevier-Biosoft) using the following equations:

$$V_s = V_0/(1+[I]/K_i^{app})$$

$$K^{app} = K_i(1-[S]/K_m)$$

where [I] and [S] are the concentrations of inhibitor and substrate, respectively, $V_0$ and $V_s$ are the velocities of aminolysis in the absence and presence of inhibitor, respectively, $K_i^{app}$ and $K_i$ are apparent and true inhibition constants, respectively, and $K_m$ is the Michaelis constant. The inhibition assays were performed and measured as described in Example 2.

What is claimed is:

1. A serine elastase inhibitor, comprising:
an agent in a pharmaceutically acceptable carrier having a chemical structure including a seine elastase recognition moiety and a warhead moiety wherein the serine elastase recognition moiety includes any of compounds 2 through 27 in FIG. 5; R$_2$ and R$_3$ are selected from the group consisting of H, phenly, cyclohexyl, and morpholino such that R$_2$ may not be the same as R$_3$ within a structure and R$_4$ is H or

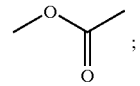

the agent providing balanced inhibitory activity with respect to a plurality of serine elastases.

2. An inhibitor according to claim 1, wherein the plurality of elastases include neutrophil elastase and PR-3.

3. An inhibitor according to claim 2, wherein inhibition of neutrophil elastase by the agent has a first inhibitory constant and inhibition of PR-3 by the agent has a second inhibitory constant such that the first and second constants differ by no more than two orders of magnitude.

4. An inhibitor according to claim 3, wherein the first and second constants differ by a factor no larger than fifty-fold.

5. An inhibitor according to claim 4, wherein the first and second constants differ by no more than one order of magnitude.

6. An inhibitor according to claim 1, wherein one of the serine elastase recognition moiety and the warhead moiety contains a carbonyl group, the serine elastase recognition moiety contains a first submoiety including an R$_1$ sidechain, the warhead moiety contains a heterocycle warhead submoiety, a carbonyl carbon of the carbonyl group directly attached to a carbon of the heterocycle warhead submoiety and to the first submoiety.

7. An inhibitor according to claim 1, wherein the serine elastase recognition moiety includes a plurality of first submoieties.

8. An inhibitor according to claim 6, wherein the first submoiety is directly attached to a carbon of the warhead moiety.

9. An inhibitor according to claim 8, wherein the serine elastase recognition moiety further includes the following structure:

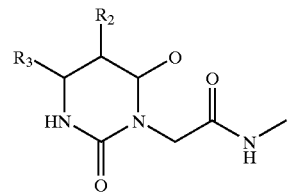

wherein R$_2$ and R$_3$ are selected from the group consisting of H, phenyl, cyclohexyl, and morpholino, such that R$_2$ may not be the same as R$_3$ within a structure.

10. An inhibitor according to claim 9, wherein the first submoiety includes an R$_1$ side chain which is selected from the group consisting of (—CH$_3$), (—CH$_2$CH$_3$), (—CH$_2$CH$_2$CH$_3$), (—CH$_2$CH$_2$CH$_2$CH$_3$), (—CH$_2$CH$_2$—S—CH$_3$), (—CH$_2$—S—CH$_3$), (—CH$_2$CH$_2$—O—CH$_3$), (—CH$_2$—O—CH$_3$), and (—CH$_2$—O—CH$_2$CH$_3$).

11. An inhibitor according to claim 8, wherein the warhead moiety is alternatively selected from the group consisting of: non-oxadiazole heterocycles including benzoxazole and substituted benzoxazole; perfluorinated alkylketones including trifluoromethyl ketone and pentafluoroethyl ketone; halomethyl ketone; and boronic acid.

12. A method of inhibiting the activity of a plurality of seine elastases, comprising: administering to an environment in which serine elastases are present, an effective amount of a compound according to claim 1.

13. A method according to claim 12, wherein a plurality of serine elastases include neutrophil elastase and PR-3.

Figure 5:
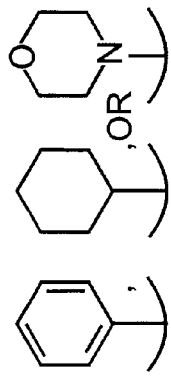
FIG. 5 illustrates alternative configurations for Z.
Figures 3, 3A, 4, 5, 6, 7, 8, 9, 10, 11, 12, 13, 14, 15, 16, 17, 18:
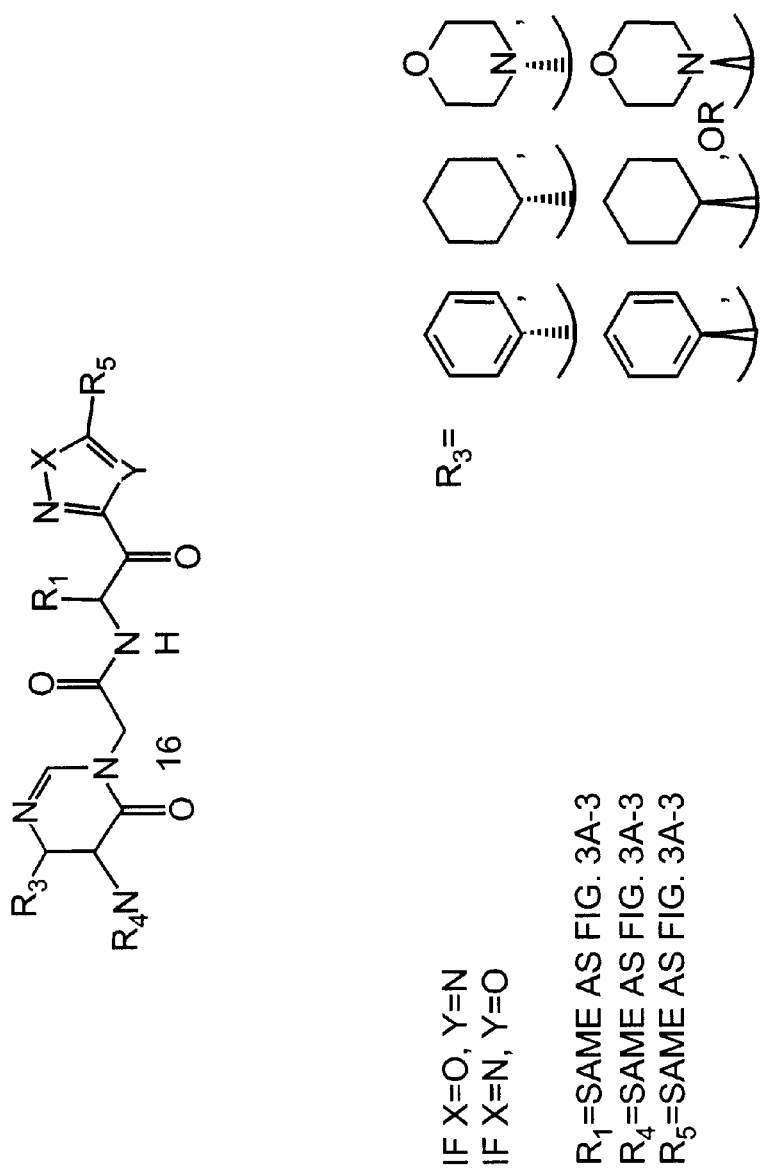
Figures 3, 3A, 4, 5, 6, 7, 8, 9, 10, 11, 12, 13, 14, 15, 16, 17, 18, 19, 20, 21, 22, 23, 24, 25, 26, 27, 28:
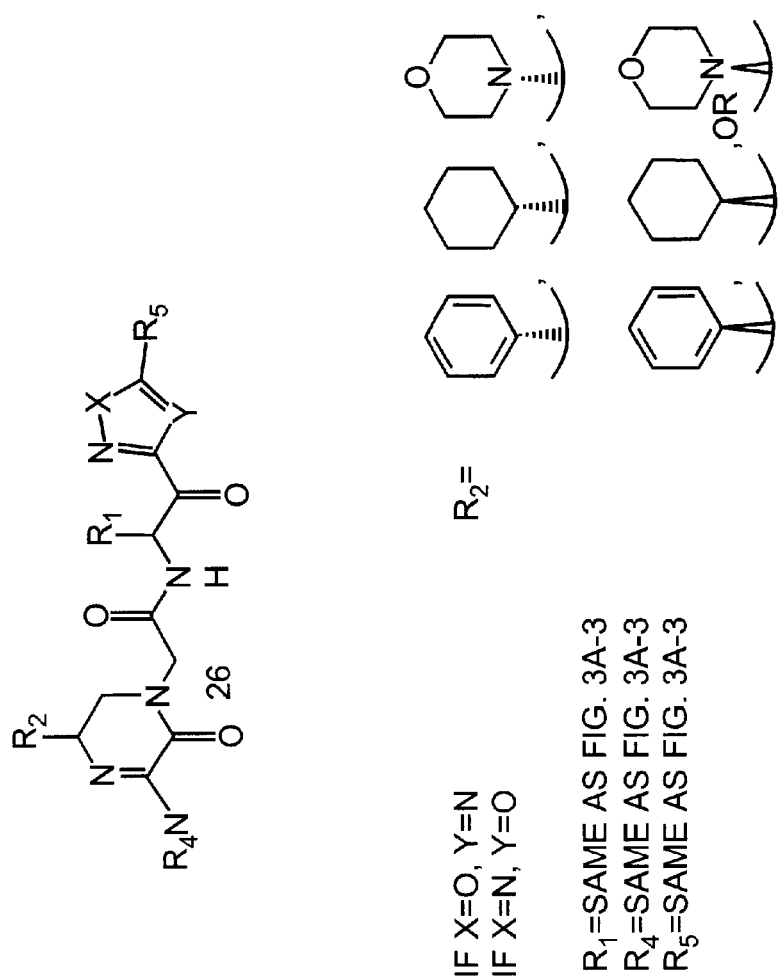
Figures 3, 3A, 4, 5, 6, 7, 8, 9, 10, 11, 12, 13, 14, 15, 16, 17, 18, 19, 20, 21, 22, 23, 24, 25, 26, 27, 28, 29:
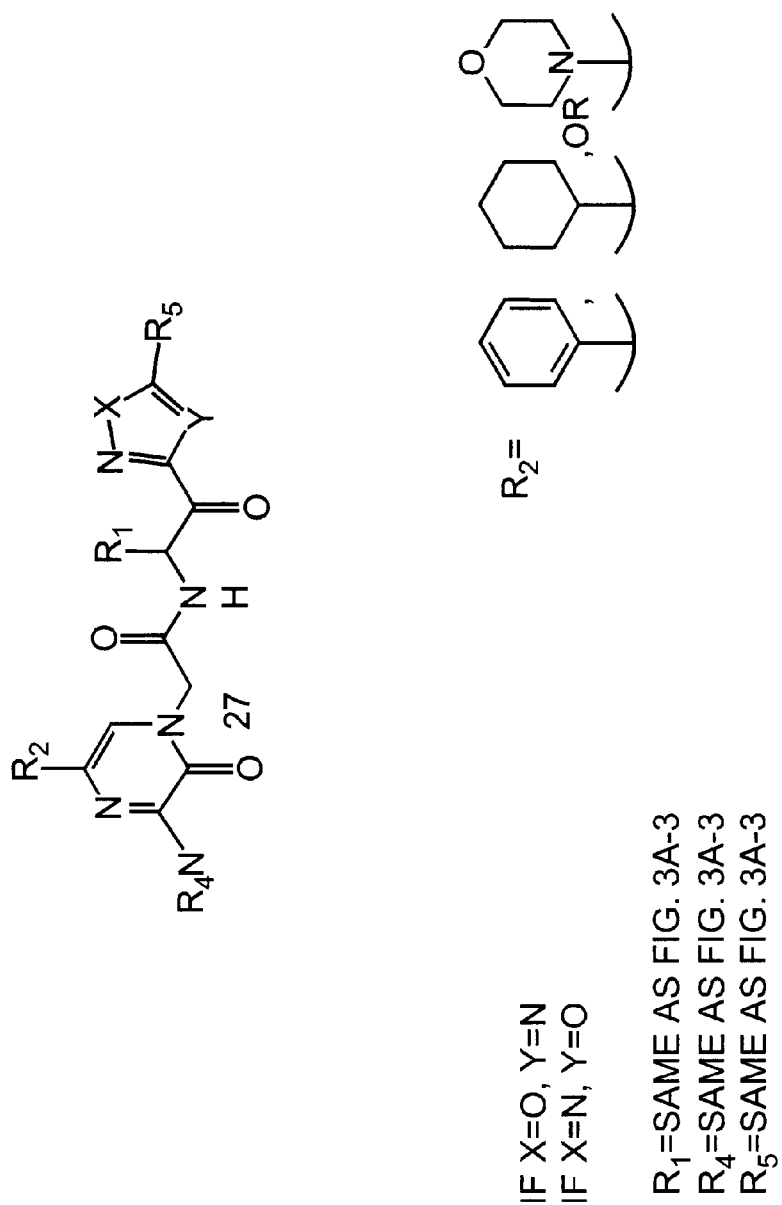
Figure 4:
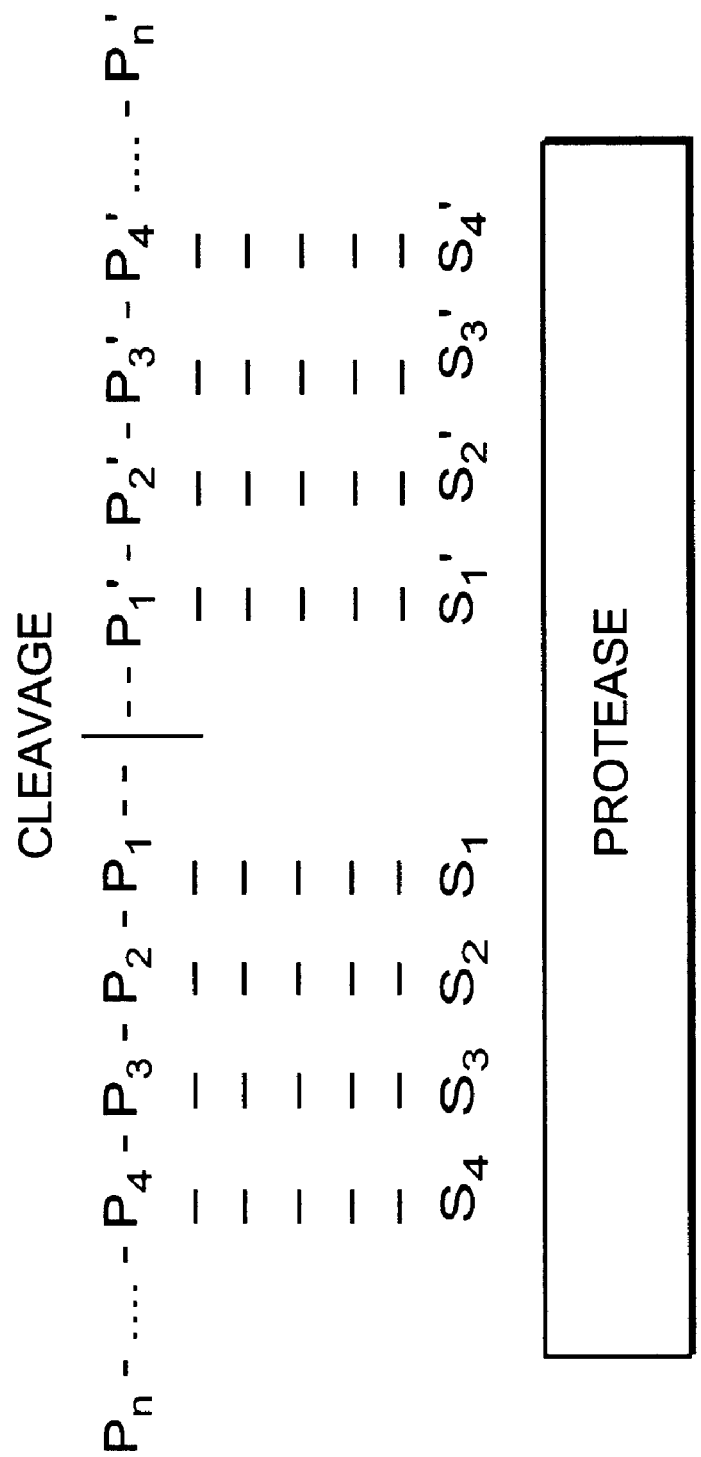
Figures 5, 5A:
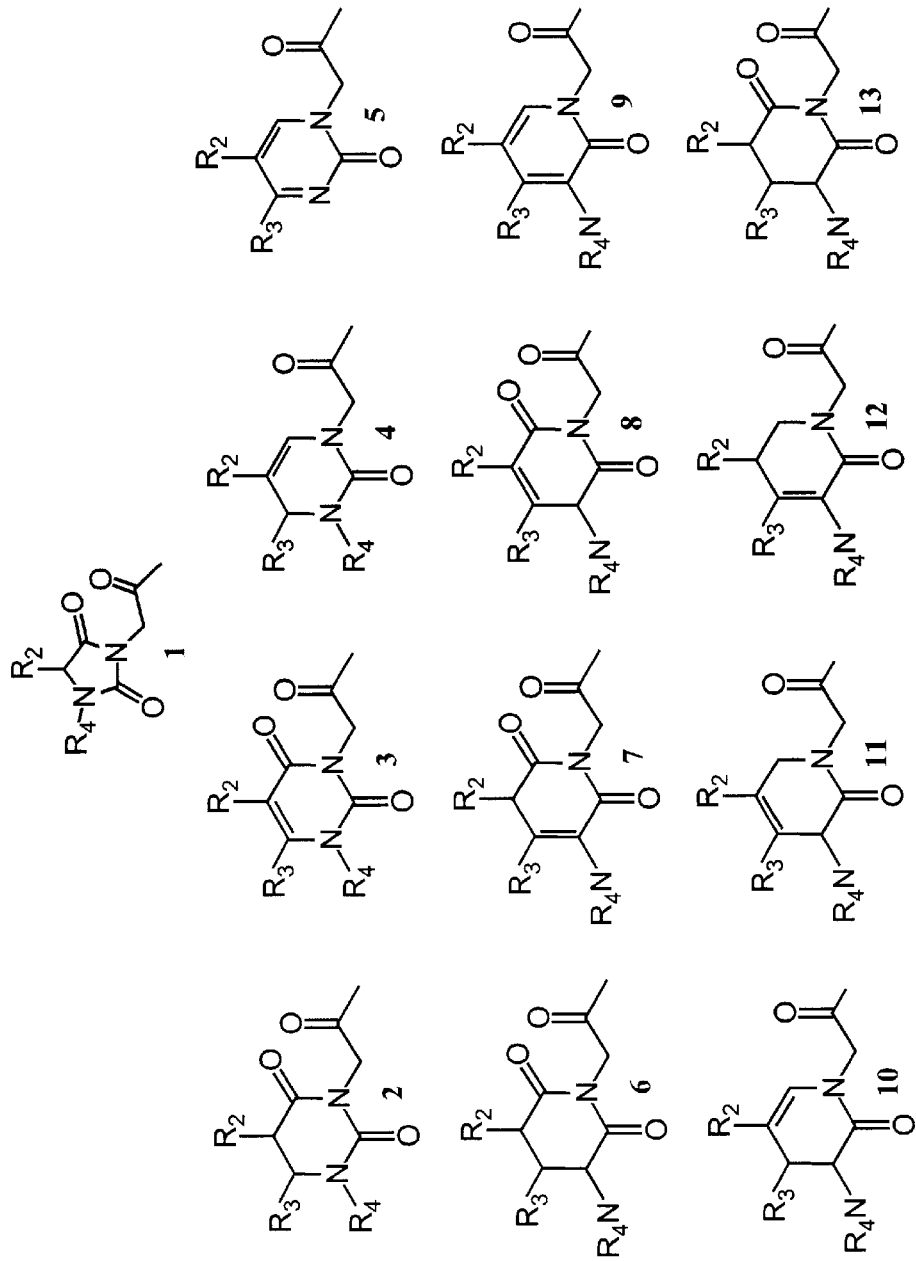
Figure 5B:
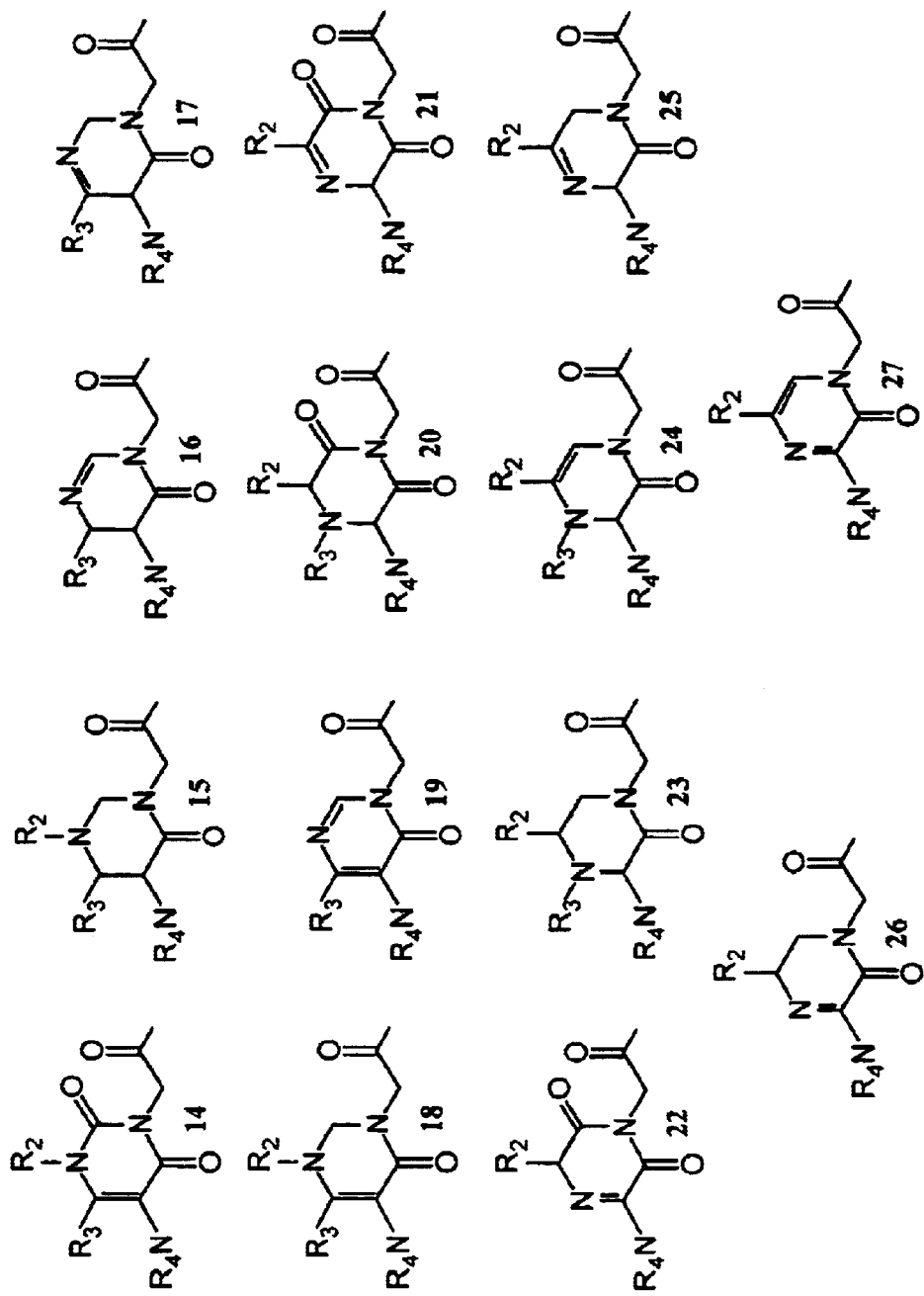

14. A compound of the formula:

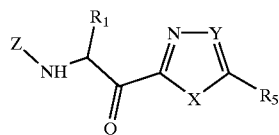

wherein Z is selected from the group consisting of any of the compounds 2–27 described in FIG. 5;

$R_1$ is selected from the group consisting of (—CH$_3$), (—CH$_2$CH$_3$), (—CH$_2$CH$_2$CH$_3$), (—CH$_2$CH$_2$CH$_2$CH$_3$), (—CH$_2$CH$_2$—S—CH$_3$), (—CH$_2$—S—CH$_3$), (—CH$_2$CH$_2$—O—CH$_3$), (—CH$_2$—O—CH$_3$), and (—CH$_2$—O—CH$_2$CH$_3$);

$R_2$ is selected from the group of phenyl, cyclohexyl, morpholino, H;

$R_4$ is H or,

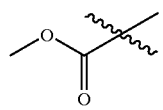

$R_5$ is selected from alkyl, alkenyl, haloalkyl, haloalkenyl, alkynyl being linear or branched; a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamido, arylcarboxamido, alkylthio, or haloalkylthio groups being linear or branched; a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamido, arylcarboxamido, alkylthio or haloalkylthio groups being linear or branched; and X and Y are independently O, S or N wherein N is optionally substituted with alkyl, alkenyl, alkynyl being linear or branched: a phenyl, phenylalkenyl, or phenylalkyl optionally substituted with halogen, cyano, nitro, haloalkyl, amino, aminoalkyl, dialkylamino, alkyl, alkenyl, alkynyl, alkoxy, haloalkoxy, carboxyl, carboalkoxy, alkylcarboxamido, arylcarboxamido, alkylthio, or haloalkylthio groups being linear or branched; a heteroaryl, heteroarylalkyl or heteroarylalkenyl wherein the heteroaryl group is a monocyclic five or six membered ring containing one or two heteroatoms independently selected from oxygen, sulfur and nitrogen optionally substituted with halogen, cyano, nitro, haloalkyl, amino, aminoalkyl, dialkylamino, alkyl, alkoxy, alkenyl, alkynyl, haloalkoxy, carboxyl, carboalkoxy, alkylcarboxamido, arylcarboxamido, alkylthio or haloalkylthio groups being linear or branched, provided at least one of X or Y is N; and provided that where both X and Y are N, only one of X or Y is substituted; and $R_1$, $R_2$, $R_3$, $R_4$ and $R_5$ further including any of the structures depicted for this group in FIGS. 3A-1 through 3A-3.

15. An inhibitor according to 14, wherein the warhead moiety is selected from the group consisting of: a non-oxadiazole heterocycle including benzoxazole and substituted benzoxazole; perfluorinated alkylketone including trifluoromethyl ketone and pentafluoroethyl ketone; halomethyl ketone, boronic acid, aldehyde, di-ketone, alpha keto acid, alpha keto ester; and active ester.

16. A pharmaceutical formulation for treating an elastase induced pathology, comprising:

an effective dose of a compound according to claim 14.

17. A method of inhibiting proteinase-3, comprising: administering to a subject in need of proteinase-3 inhibition, an effective amount of a compound according to claim 14 in a pharmaceutically acceptable formulation.

18. A method of inhibiting neutrophil elastase, comprising: administering to a subject in need of neutrophil elastase inhibition, an effective amount of a compound according to claim 14 in a pharmaceutically acceptable formulation.

19. A method according to claim 17, further comprising: administering to a subject in need of neutrophil elastase and proteinase-3 inhibition, an effective amount of the compound in a pharmaceutically acceptable formulation so as to inhibit both proteinase-3 and neutrophil elastase.

20. An inhibitor according to claim 1, wherein the plurality of elastases includes at least one of endovascular elastase or endothelial elastase.

21. A method according to claim 11, wherein the plurality of elastases includes at least one of endovascular elastase or endothelial elastase.

* * * * *

UNITED STATES PATENT AND TRADEMARK OFFICE
CERTIFICATE OF CORRECTION

PATENT NO. : 6,777,403 B2
DATED : August 17, 2004
INVENTOR(S) : John C. Cheronis It is certified that error appears in the above-identified patent and that said Letters Patent is hereby corrected as shown below:

Column 14,
Line 14, delete "R1, R2, R3, R4 and"

Signed and Sealed this

Twenty-sixth Day of October, 2004

JON W. DUDAS
*Director of the United States Patent and Trademark Office*